United States Patent [19]
Cheshire et al.

[11] Patent Number: 6,143,751
[45] Date of Patent: Nov. 7, 2000

[54] PYRIDINE DERIVATIVES AND PHARMACEUTICAL COMPOSITIONS CONTAINING THEM

[75] Inventors: David Cheshire, Nottingham; David Cladingboel, Leics; Martin Cooper, Leics; David Hardern, Leics; Simon Hirst, Notts; Carol Manners; Michael Stocks, both of Nottingham, all of United Kingdom

[73] Assignee: AstraZeneca UK Limited, London, United Kingdom

[21] Appl. No.: 09/068,521

[22] PCT Filed: Mar. 27, 1998

[86] PCT No.: PCT/SE98/00575

§ 371 Date: May 11, 1998

§ 102(e) Date: May 11, 1998

[87] PCT Pub. No.: WO98/43971

PCT Pub. Date: Oct. 8, 1998

[30] Foreign Application Priority Data

| Apr. 1, 1997 | [SE] | Sweden | 9701194 |
| Jun. 9, 1997 | [SE] | Sweden | 9702200 |
| Nov. 28, 1997 | [SE] | Sweden | 9704402 |

[51] Int. Cl.[7] .............. A61K 31/505; A61K 31/44; C07D 401/00; C07D 213/28; C07D 409/00

[52] U.S. Cl. ............ 514/274; 514/274; 514/275; 514/277; 514/332; 514/335; 514/336; 514/337; 514/338; 514/340; 514/341; 514/342; 544/310; 544/331; 544/333; 546/256; 546/261; 546/264; 546/266; 546/268.4; 546/276.1; 546/280.4; 546/281.7; 546/282.4; 546/285

[58] Field of Search .................. 514/274, 275, 514/277, 332, 335, 336, 337, 338, 341, 340, 342; 544/310, 331, 333; 546/256, 261, 264, 266, 268.4, 282.4, 281.7, 280.4, 285, 276.1

[56] References Cited

U.S. PATENT DOCUMENTS 5,977,105  11/1999  Cheshire et al. .................. 514/241

FOREIGN PATENT DOCUMENTS 0 264 114 A1  4/1988  European Pat. Off. .
0 267 439 A2  5/1988  European Pat. Off. .
97/20815     6/1997  WIPO .

*Primary Examiner*—Mukund J. Shah
*Assistant Examiner*—Ben Schroeder
*Attorney, Agent, or Firm*—Nixon & Vanderhye

[57] ABSTRACT

Compounds of the formula (I) wherein X, $R^1$, $R^2$, and $Ar^1$ as defined in the specification. The compounds are useful medicaments, particularly in the treatment of asthma or rhinitis.

11 Claims, No Drawings

PYRIDINE DERIVATIVES AND PHARMACEUTICAL COMPOSITIONS CONTAINING THEM

This invention relates to novel pyridyl derivatives, their use as medicaments, pharmaceutical formulations including them and methods for their preparation.

European Patent Applications EP-A-0 264 114 and EP-A-0 267 439 disclose certain phenylalkyl- and phenylalkoxypyridine alkanol derivatives and their use as platelet-activating factor (PAF) antagonists.

A series of structurally distinct compounds have now been found to be useful for the modulation of inflammatory conditions. In a first aspect the present invention therefore provides a compound of formula I:

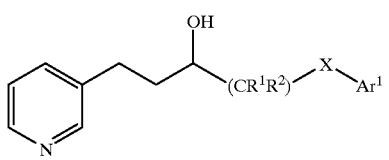

(I)

wherein;

X is O, S or $CH_2$;

$R^1$ and $R^2$ are independently hydrogen, $C_{1-6}$ alkyl or $C_{3-6}$ cycloalkyl or $R^1$ and $R^2$ together with the carbon atom to which they are attached form a $C_{3-6}$ cycloalkyl group;

$Ar^1$ is a fused bicyclic ring system containing one or more heteroatoms, a fused tricyclic ring system optionally containing an oxygen atom, or $Ar^1$ is a group $R^3$–$R^4$ where one of $R^3/R^4$ is a phenyl ring and the other is a 5- or 6-membered heterocyclic ring containing one or more heteroatoms, each $Ar^1$ group being optionally substituted by halo, nitro, $C_{1-6}$ alkyl (optionally substituted by one or more fluorine atoms), CN, —Y—$NR^6C(O)NR^7$—$R^8$, —O—Y—$C(O)NR^7R^8$, —O—Y—$C(S)NR^7R^8$, —Y—$C(O)NR^7R^8$, —Y—$C(S)NR^7R^8$, —Y—$SO_2NR^7R^8$, —Y—$NR^7R^8$, $SO_2NR^7R^8$, $C(O)NR^7R^8$, $C(S)NR^7R^8$, $C(O)R^9$, —OC(O)$R^9$, —Y—$OR^9$, —Y—$CO_2R^9$, —Y—$NR^{10}C(O)NR^{11}$—Z—$R^{12}$, $SO_2NR^{10}C(O)NR^7R^8$, —Y—$SO_2NHNR^7R^8$, —Y—$C(O)NR^{11}$—Z—$R^{12}$, —Y—$C(S)NR^{11}$—Z—$R^{12}$, $N(R^{10})SO_2R^{11}$, $N(R^{10})C(O)R^{11}$ or $N(R^{10})CO_2R^{11}$ where:

Y is a bond, $C_{1-6}$ alkylene or $C_{2-6}$ alkenylene;

$R^7$ and $R^8$ are independently hydrogen or $C_{1-6}$ alkyl or together with the nitrogen atom to which they are attached form an optionally substituted 5- to 7-membered heterocyclic ring optionally containing a further heteroatom selected from nitrogen, oxygen or sulfur;

$R^5$, $R^6$, $R^9$, $R^{10}$ and $R^{11}$ are independently hydrogen or $C_{1-10}$ alkyl (optionally substituted by one or more fluorine atoms);

Z is $C_{1-6}$ alkylene; and $R^{12}$ is a group $NR^{10}C(O)R^{11}$, $NR^{10}CO_2R^{11}$, $OR^5$, $NR^7R^8$ or $CO_2R^{13}$ where $R^5$, $R^7$, $R^8$, $R^{10}$ and $R^{11}$ are as defined above and $R^{13}$ is hydrogen, $C_{1-6}$ alkyl, $C_{1-6}$ alkylaryl or aryl optionally substituted by hydroxy, or a salt or solvate thereof.

Alkyl, alkylene and alkenylene groups, whether alone or part of another group, can be straight chained or branched and can be optionally substituted by one or more fluorine atoms and optionally interrupted by one or more oxygen atoms.

Suitably X is O, S or $CH_2$. Preferably X is O.

Suitably $R^1$ and $R^2$ are independently hydrogen, $C_{1-6}$ alkyl or $C_{3-6}$ cycloalkyl or $R^1$ and $R^2$ together with the carbon atom to which they are attached form a $C_{3-6}$ cycloalkyl group. Preferably $R^1$ and $R^2$ are both hydrogen or one is hydrogen and the other is methyl.

Suitably $Ar^1$ is a fused bicyclic ring system containing one or more heteroatoms, a fused tricyclic ring system optionally containing an oxygen atom, or $Ar^1$ is a group $R^3$—$R^4$ where one of $R^3/R^4$ is a phenyl ring and the other is a 5- or 6-membered heterocyclic ring containing one or more heteroatoms, each $Ar^1$ group being optionally substituted by halo, nitro, $C_{1-6}$ alkyl (optionally substituted by one or more fluorine atoms), CN, —Y—$NR^6C(O)NR^7$—$R^8$, —O—Y—$C(O)NR^7R^8$, —O—Y—$C(S)NR^7R^8$, —Y—$C(O)NR^7R^8$, —Y—$C(S)NR^7R^8$, —Y—$SO_2NR^7R^8$, —Y—$NR^7R^8$, $SO_2NR^7R^8$, $C(O)NR^7R^8$, $C(S)NR^7R^8$, $C(O)R^9$, —OC(O)$R^9$, —Y—$OR^9$, —Y—$CO_2R^9$, —Y—$NR^{10}C(O)NR^{11}$—Z—$R^{12}$, $SO_2NR^{10}C(O)NR^7R^8$, —Y—$SO_2NHNR^7R^8$, —Y—$C(O)NR^{11}$—Z—$R^{12}$, —Y—$C(S)NR^{11}$—Z—$R^{12}$, $N(R^{10})SO_2R^{11}$, $N(R^{10})C(O)R^{11}$ or $N(R^{10})CO_2R^{11}$ where Y is a bond, $C_{1-6}$ alkylene or $C_{2-6}$ alkenylene. More than one substituent can be present. Preferred substituents are those exemplified herein.

When $Ar^1$ is a fused bicyclic ring system containing one or more heteroatoms such rings can be 6,6 or 6,5 ring systems and can be partially saturated or saturated. Examples of such rings include benzofuran, benzothiphene and benzo-1,4-dioxan rings. Examples of suitable fused tricyclic ring systems include 6,5,6 ring systems such as fluorene and dibenzofuran rings. When $Ar^1$ is a group $R^3$—$R^4$ suitable heterocyclic rings include thiophene, pyridyl, pyrimidine and pyridone rings. Preferably $Ar^1$ is a group $R^3$—$R^4$ where $R^3$ is phenyl and $R^4$ is thiophene substituted by cyano, halo, methyl or sulphonamido.

Particularly preferred compounds of the invention include:

(±)-1-(2,3-Dihydro-benzo[1,4]dioxin-6-yl)-5-pyridin-3-yl-pentan-3-ol, (±)-1-(2,3-Dihydro-benzo[1,4]dioxin-6-yloxy)-4-pyridin-3-yl-butan-2-ol, (±)-1-([9H]-Fluoren-2-yloxy)-4-pyridin-3-yl-butan-2-ol, (±)-1-(Dibenzofuran-3-yloxy)-4-pyridin-3-yl-butan-2-ol, (2R)-1-[4-(5-Chloro-thiophen-2-yl)-phenoxy]-4-pyridin-3-yl-butan-2-ol, (±)-1-(Benzofuran-6-yloxy)-4-pyridin-3-yl-butan-2-ol, (2R)-5-[4-(2-Hydroxy-4-pyridin-3-yl-butoxy)-phenyl]-1,3-dimethyl-1H-pyrimidine-2,4-dione, (2R)-1-[4-(2,4-Dimethoxy-pyrimidin-5-yl)-phenoxy]-4-pyridin-3-yl-butan-2-ol, (2R)-5-[4-(2-Hydroxy-4-pyridin-3-yl-butoxy)-phenyl]-1H-pyrimidine-2,4-dione, (2R)-4-[4-(2-Hydroxy-4-pyridin-3-yl-butoxy)phenyl]-1H-pyrimidin-2-one, (2R)-5-[4-(2-Hydroxy-4-pyridin-3-yl-butoxy)-phenyl]-1H-pyrimidin-2-one, (2R)-4-[4-(2-Hydroxy-4-pyridin-3-yl-butoxy)-phenyl]-1-methyl-1H-pyridin-2-one, (2R)-5-[4-(2-Hydroxy-4-pyridin-3-yl-butoxy)phenyl]-1-methyl-1H-pyridin-2-one, (2R)-1-(4-[1,3,4]-Oxadiazol-2-ylphenoxy)-4-pyridin-3-yl-butan-2-ol, (2S,3R)-2-(4-(2,4-Dimethoxypyrimidin-5-yl)phenoxy)-5-pyridin-3-yl-pentan-3-ol, (1S,2R)-5-[4-(2-Hydroxy-1-methyl-4-pyridin-3-yl-butoxy)-phenyl]-1H-pyridin-2-one,
(1S,2R)-5-[4-(2-Hydroxy-1-methyl-4-pyridin-3-yl-butoxy)phenyl]-1-methyl-1H-pyridin-2-one,
(3R,4S)-4-[4-(6-Dimethylaminopyridin-2-yl)-phenoxy]-1-pyridin-3-ylpentan-3-ol,
(2R)-1-[4-(6-Dimethylaminopyridin-2-yl)-phenoxy]-4-pyridin-3-ylbutan-2-ol,
(2R)-5-[4-(2-Hydroxy-4-pyridin-3-ylbutoxy)phenyl]thiophene-2-sulfonic acid amide, (1S, 2R)-5-[4-(2-Hydroxy-1-methyl-4-pyridin-3-yl-butoxy)-phenyl]-thiophene-2-sulfonic acid amide,
(3R,4S)-4-[4-(2-Methoxypyridin-3-yl)phenoxy]-1-pyridin-3-yl-pentan-3-ol,
(3R,4S)-4-[4-(2-Dimethylaminopyridin-3-yl)phenoxy]-1-pyridin-3-ylpentan-3-ol,
(3R,4S)-4-[4-(2-Methoxypyridin-4-yl)phenoxy]-1-pyridin-3-yl-pentan-3-ol,
(1S,2R)-5-[4-(2-Hydroxy-1-methyl-4-pyridin-3-yl-butoxy)phenyl]nicotinonitrile,
(2R)-5-[4-(2-Hydroxy-4-pyridin-3-yl-butoxy)phenyl] nicotinonitrile,
(3R,4S)-4-[4-(6-Methoxy-pyridin-2-yl)-phenoxy]-1-pyridin-3-yl-pentan-3-ol,
(2R)-1-[4-(6-Methoxy-pyridin-2-yl)-phenoxy]-4-pyridin-3-yl-butan-2-ol,
(1S,2R)-4-[4-(2-Hydroxy-1-methyl-4-pyridin-3-yl-butoxy)phenyl]-(1H)-pyridin-2-one,
(3R,4S)-4-(4-[1,3,4]Oxadiazol-2-ylphenoxy)-1-pyridin-3-yl-pentan-3-ol,
(2R)-4-[4-(2-Hydroxy-4-pyridin-3-yl-butoxy)-phenyl]-(1H)-pyridin-2-one,
(1R,2S)-4-[4-(2-Hydroxy-1-methyl-4-pyridin-3-yl-butoxy)-phenyl]pyrazole-1-sulfonic acid dimethylamide,
(2R)-1-[4-(2-Methoxypyridin-3-yl)phenoxy]-4-pyridin-3-ylbutan-2-ol,
(2R)-4-Pyridin-3-yl-1-(4-pyrimidin-5-yl-phenoxy)butan-2-ol,
(3R,4S)-1-Pyridin-3-yl-4-(4-pyrimidin-5-yl-phenoxy)pentan-3-ol,
(1S,2R)-5-[4-(2-Hydroxy-1-methyl-4-pyridin-3-yl-butoxy)-phenyl]-1-methyl-3-trifluoromethyl-1H-pyridin-2-one,
(2R)-5-[4-(2-Hydroxy-4-pyridin-3-yl-butoxy)-phenyl]-1-methyl-3-trifluoromethyl-1H-pyridin-2-one,
(3R,4S)-4-[4-(4-Chloro-2-methylamino-pyrimidin-5-yl)-phenoxy]-1-pyridin-3-yl-pentan-3-ol,
(2S)-5(4-(2-Hydroxy-4-pyridin-3-yl-butoxy)phenyl) thiophene-2-sulfonic acid amide,
(1S,2R)-5-Chloro-3-[4-(2-hydroxy-1-methyl-4-pyridin-3-yl-butoxy)-phenyl]-1H-pyridin-2-one,
(2R)-5(4-(2-Hydroxy-4-pyridin-3-yl-butanthio)phenyl) thiophene-2-sulfonic acid amide,
(1S,2R)-4-[4-(2-Hydroxy-1-methyl-4-pyridin-3-yl-butoxy)-phenyl]-thiophene-2-sulfonic acid amide,
or salts or solvates thereof.

Compounds of the invention can form pharmaceutically acceptable solvates and salts. The compounds of the formula (I) can form acid addition salts with acids, such as conventional pharmaceutically acceptable acids, for example maleic, hydrochloric, hydrobromic, phosphoric, acetic, fumaric, salicylic, citric, lactic, mandelic, tartaric, trifluoroacetic and methanesulphonic acids. Compounds of the invention may also form alkali metal salts such as magnesium, sodium, potassium and calcium salts.

Certain compounds of formula (I) are capable of existing in stereoisomeric forms including enantiomers and the invention extends to each of these stereoisomeric forms and to mixtures thereof including racemates. The different stereoisomeric forms may be separated one from the other by the usual methods, or any given isomer may be obtained by stereospecific or asymmetric synthesis. The invention also extends to any tautomeric forms and mixtures thereof.

According to the invention there is also provided a process for the preparation of compounds of formula (I) as hereinbefore defined which comprises:

(a) reduction of a corresponding compound of formula (II):

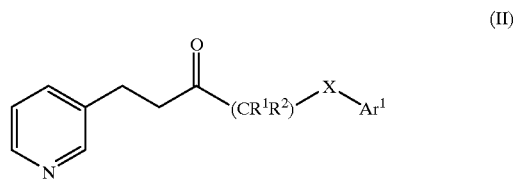

(II)

wherein $R^1$, $R^2$, X and $Ar^1$ is as defined in formula (I);

(b) for compounds of formula (I), wherein $Ar^1$ is a group $R^3$—$R^4$, forming the $R^3$—$R^4$ bond by reaction of a compound of formula (III):

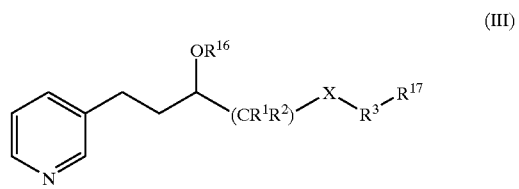

(III)

with a compound of formula (IV):

(IV)

$R^4$——$R^{18}$ where $R^1$, $R^2$, $R^3$, $R^4$ and are as defined in formula (I), $R^{16}$ is a hydroxy protecting group, and one of $R^{17}/R^{18}$ is triflate or halo and the other is $B(OH)_2$, or ZnHal, or (c) for compounds of formula (I) where $R^1$ and $R^2$ are both hydrogen, reaction of (±)-3-(2-oxiranylethyl) pyridine or α-(chloromethyl)-3-pyridinepropanol either with a compound of formula (V):

$MYAr^1$ (V)

where Y is O, S or $CH_2$, M is Li, Na, K, Cs or MgHal where Hal is halogen and $Ar^1$ is as defined in formula (I);

or with a compound of formula (VI):

$HYAr^1$ (VI)

where Y is as defined in formula (V) in the presence of a base; or (d) for compounds of formula (I), where $R^1$ and $R^2$ are both hydrogen, and X represents O or S, reaction of a compound of formula (V) or (VI), as hereinbefore defined, with a suitably protected and activated derivative of 4-(3-pyridyl)-1,2-butanediol; or (e) preparation of compounds of formula (I) wherein X represents O, from a compound of formula (VII):

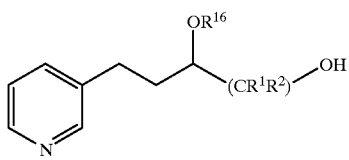

(VII)

in which $R^3$, $R^4$, and $R^{16}$ are as defined in process (b) by reaction with a compound of formula (VI) wherein Y represents O, and optionally thereafter process (a) to (e):

removing any protecting groups forming a pharmaceutically acceptable salt or solvate.

Reduction of a compound of formula (II) can be carried out with a suitable reducing agent (e.g. sodium borohydride) for example at room temperature in the presence of a suitable organic solvent (e.g. ethanol).

Reaction of compounds of formulae (III) and (IV) can be carried out under the conditions of the Suzuki reaction (*Synthetic Communications* 11(7), 513–519, 1981) for example at 100° C. in the presence of a suitable catalyst and base (e.g. tetrakis(triphenylphosphine)palladium(0) and aqueous sodium carbonate) in a suitable solvent (e.g. ethanol/toluene).

Reaction of (±)-3-(2-oxiranylethyl)pyridine or α-(chloromethyl)-3-pyridinepropanol either with a compound of formula (VI) can be carried out in the presence of a base such as sodium hydroxide in a suitable solvent such as aqueous ethanol.

Process (c) is carried out at ambient or reduced temperature in a suitable solvent such as dimethylformamide or tetrahydrofuran.

Process (d) is carried out at elevated temperature, for example at about 60° C., in the presence of suitable base (e.g. sodium hydride) and an appropriate organic solvent (e.g. dimethylformamide). Suitably protected and activated derivative of 4-(3-pyridyl)-1,2-butanediol for example the compound (VIII):

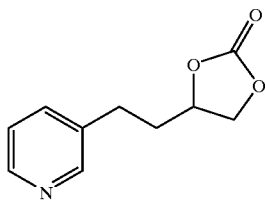

(VIII)

Processes (e) is carried out under the conditions of the Mitsonobu reaction, for example at approximately 0–25° C. in the presence of diethyl azodicarboxylate and triphenylphosphine in an appropriate solvent (e.g. toluene).

Compounds of formula (III) wherein $R^{17}$ is B(OH)$_2$, can be prepared from a compound in which $R^{17}$ is bromine or iodine by, for example, treatment with n-butyllithium and triisopropylborate in an appropriate solvent (e.g. tetrahydrofuran), at low temperature (e.g. −78° C.).

An alternative preparation of compounds of formula (III) wherein X represents O is from compounds of formula (VII) as defined above by reaction with a compound of formula (IX), in which $R^{17}$ is triflate, or halogen:

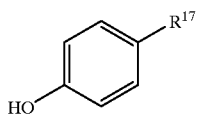

(IX)

under the conditions of the Mitsonobu reaction as described above.

Compounds of formula (VII) can be prepared by reduction of a compound of formula (X)

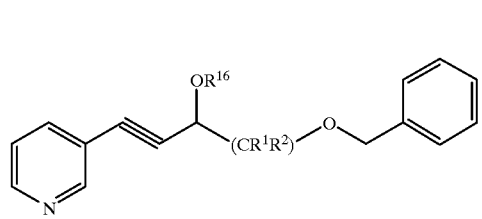

(X)

in which $R^1$, $R^2$ and $R^{16}$ are as defined above using conventional procedures, for example hydrogenation using a palladium catalyst in an inert solvent such as ethyl acetate, followed by debenzylation using conventional methods such as those described in 'Protective Groups in Organic Synthesis', 2$^{nd}$ Edition, T. W. Greene & P. G. M. Wuts, Wiley-Interscience (1991).

Compounds of formula (X) can be prepared by the reaction of compound (XI):

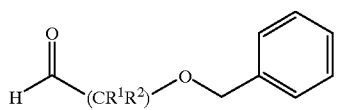

(XI)

reported by Reetz. et. al. *Angew. Chem. Suppl.*, (1983), 1511.) in which $R^1$ and $R^2$ are as defined above with a compound of formula (XII):

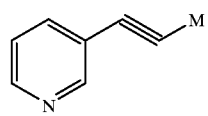

(XII)

in which M is lithium, sodium, potassium, MgX or ZnX, where X is halogen, optionally in the presence of additives such as boron trifluoride.

It will be appreciated by those skilled in the art that in the process described above the functional groups of intermediate compounds may need to be protected by protecting groups.

Functional groups which it is desirable to protect include hydroxy, amino and carboxylic acid. Suitable protecting groups for hydroxy include organosilyl groups (e.g. tert-butyldimethylsilyl, tert-butyldiphenylsilyl or trimethylsilyl), benzyl and tetrahydropyranyl. Suitable protecting groups for amino include tert-butoxycarbonyl or benzyloxy carbonyl. Suitable protecting groups for carboxylic acid include $C_{1-6}$ alkyl or benzyl esters. The protection and deprotection of functional groups may take place before or after a reaction step.

The use of protecting groups is fully described in 'Protective Groups in Organic Chemistry', edited by J. W. F. McOmie, Plenum Press (1973), and 'Protective Groups in Organic Synthesis', 2nd edition, T. W. Greene & P. G. M. Wutz, Wiley-Interscience (1991).

Novel intermediates form a further aspect of the invention.

Diastereoisomers may be separated using conventional techniques, e.g. chromatography or fractional crystallisation. The various optical isomers may be isolated by separation of a racemic or other mixture of the compounds using conventional, e.g. fractional crystallisation or HPLC, techniques.

The compounds of the invention are useful because they possess pharmacological activity and more particularly activity in the modulation of inflammatory and allergic conditions, for example as shown in the test described below. The compounds of the invention inhibit the activation of a range of cell types from haematopoetic lineage, including mast cells, neutrophils and eosinophils. In a further aspect the invention therefore provides a compound of formula (I) or a pharmaceutically acceptable salt or solvate thereof for use in therapy.

The compounds of the invention are indicated for use in the treatment or prevention of allergic, inflammatory, autoimmune, proliferative and hyper-proliferative diseases.

The compounds of the invention are also indicated in the treatment and prevention of allergic, inflammatory or auto-immune conditions of the lung, including reversible obstructive airways diseases which includes asthma (e.g. bronchial, allergic, intrinsic asthma, extrinsic and chronic asthma), and associated manifestations of the disease (late responses, hyper-responsiveness), also farmer's lung and related diseases, fibrosis, ideopathic interstitial pneumonia, chronic obstructive airways disease (COPD), bronchiectasis, cystic fibrosis, eosinophilic pneumonias, adult respiratory distress syndrome (ARDS), emphysema and alveolitis, for example cryptogenic fibrosing alveolitis.

Further, the compounds of the invention are indicated in the treatment or prevention of allergic, inflammatory or auto-immune conditions in the nose including all conditions characterised by inflammation of the nasal mucous membrane such as acute rhinitis, allergic rhinitis, atrophic rhinitis, chronic rhinitis including rhinitis caseosa, hypertrophic rhinitis, rhinitis purulenta and rhinitis sicca, rhinitis medicamentosa, membranous rhinitis including croupous, fibrinous and pseudomembranous rhinitis, scrofulous rhinitis, seasonal rhinitis including rhinitis nervosa (hay fever) and vasomotor rhinitis. Of particular interest are allergic rhinitis and seasonal rhinitis including rhinitis nervosa (hay fever). The compounds are also indicated for the treatment of nasal polyps and allergic menifestations of the nasopharynx other than those described hereintofore.

The compounds of the invention are also indicated the treatment or prevention of allergic, inflammatory or auto-immune conditions of the eye such as conjunctivitis (allergic, acute, vernal, of hay fever, chronic), inflammation disorders of the eyelids, cornea, uveal tract and retina.

The compounds of the invention are also indicated in the treatment and prevention of allergic, inflammatory and auto-immune conditions of the gastrointestinal tract such as food allergy and food intolerance, ulcerative colitis, Crohn's disease, irritable bowel disease, gastric ulcers, and food related allergic diseases which have symptomatic manifestations remote from the gastrointestinal tract, for example migraine, rhinitis and eczema.

The compounds of the invention are indicated for use in the treatment or prevention of allergic, inflammatory or auto-immune conditions of the skin such as psoriasis, atopical dermatitis, contact dermatitis/dermatitis herpetiformis, erythema nodosum, urticaria, cutaneous eosinophilias, acne, Alopecia areata, eosinophilic fascitis dermatomyositis, photoallergic sensitivity and periodontal disease.

The compounds of the invention are therefore indicated for use in the treatment or prevention of allergic, inflammatory or auto-immune conditions of the joints and connective tissue, including osteoarthritis, rheumatoid arthritis, systemic lupus erythematosis, vasculitis, Wegener's granulomatosis, polyarthritis nodosa, bursitis, tendonitis, gout, Behcet's syndrome, ankylosing spondits, Reiter's syndrome and psoriatic arthritis.

The compounds of the invention are indicated in the treatment and prevention of allergic, inflammatory, and auto-immune conditions of the circulatory system including atheroma, reperfusion injury (e.g. on angioplasty), myocardial infarction, thrombosis and vascular and tissue damage caused by ischaemic disease or injury.

The compounds of the invention are indicated in the treatment and prevention of allergic, inflammatory or auto-immune conditions of the CNS including Parkinson's disease, Alzheimers and other dementias, stroke and sub-arachnoid haemorrhage. The compounds of the invention are indicated in the treatment and prevention of inflammatory conditions of the liver for example hepatitis, cirrhosis and glomerulonephritis.

The compounds of the invention are indicated in the treatment and prevention of allergic, inflammatory or auto-immune conditions of the bladder and uro-genital tract including cystitis.

The compounds of the invention are indicated in the treatment and prevention of tumours and other proliferative diseases.

Of particular interest amongst the above indications is use of the compounds of the invention in a reversible obstructive airways disease, most particularly asthma and especially the treatment and prophylaxis of asthma and rhinitis.

According to a further aspect of the invention there is thus provided the use of a compound of formula I, as hereinbefore defined, or a pharmaceutically acceptable salt or solvate thereof in the manufacture of a medicament for the treatment of the above diseases, in particular reversible obstructive airways disease.

Administration of the compounds of the invention may be topical (for example by inhalation to the lung). The compounds of the invention may be inhaled as a dry powder which may be pressurised or non-pressurised.

In non-pressurised powder compositions, the active ingredient in finely divided form may be used in admixture with a larger sized pharmaceutically acceptable inert carrier.

The composition may alternatively be pressurised and contain a compressed gas, e.g. nitrogen, or a liquefied gas propellant. In such pressurised compositions, the active ingredient is preferably finely divided. The pressurised composition may also contain a surface active agent. The pressurised compositions may be made by conventional methods. The compounds of the invention may be administered systemically (for example by oral administration to the gastrointestinal tract). The active ingredient may be formulated together with known adjuvants, diluents or carriers using conventional techniques to produce tablets or capsules for oral administration to the gastrointestinal tract.

Examples of suitable adjuvants, diluents or carriers for oral administration in the form of tablets, capsules and dragees include microcrystalline cellulose, calcium phosphate, diatomaceous earth, a sugar such as lactose, dextrose or mannitol, talc, stearic acid, starch, sodium bicarbonate and/or gelatin.

According to a further aspect of the invention there is provided a pharmaceutical composition including a compound of formula I or a salt or solvate thereof as hereinbefore defined in association with a pharmaceutically acceptable adjuvant, diluent or carrier.

Suitable doses for such oral administration are in the range from 0.3 to 30 mg kg$^{-1}$ day$^{-1}$, for example 3 mg kg$^{-1}$ day$^{-1}$.

According to a further aspect of the present invention, there is provided a method of treatment or prophylaxis of a reversible obstructive airways disease, in particular asthma, which method comprises administration of a therapeutically effective amount of a compound of formula I as hereinbefore defined, or a pharmaceutically acceptable derivative thereof, to a person suffering from, or susceptible to, the disease.

It will be understood by those skilled in the art that certain functional groups in the compounds of the invention may be protected using appropriate protecting groups as hereinbefore described to form "protected derivatives" of compounds of the invention. It will also be appreciated that, although such protected derivatives may not possess pharmacological activity as such, they may be administered and thereafter metabolised in the body to form compounds of the invention which are pharmacologically active. Such derivatives may therefore be described as "prodrugs". All protected derivatives and prodrugs of compounds of formula I are included within the scope of the invention.

The invention is illustrated by the following Examples.

EXAMPLE 1
(±)-1-(2,3-Dihydro-benzo[1,4]dioxin-6-yl)-5-pyridin-3-yl-pentan-3-ol

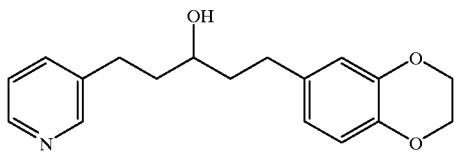

a) (±)-5-(Pyridin-3-yl)-1-penten-3-ol

Vinyl magnesium bromide (1.0 M in tetrahydrofuran, 40 ml) was added dropwise with stirring under nitrogen, to a solution of 3-(pyridin-3-yl)-1-propionaldehyde (2.70 g; see Example 3 of International Patent Application WO-A-92/19593) in tetrahydrofuran (50 ml) at 0° C. Once addition was complete the reaction was stirred at room temperature for 1 hour before being poured into saturated aqueous ammonium chloride. The mixture was extracted with dichloromethane, and the combined extracts were dried over anhydrous magnesium sulfate, filtered and concentrated under reduced pressure. The residue was purified by column chromatography over silica eluting with dichloromethane:acetone (4:1) to give the sub-title alcohol as an oil (1.80 g).

MS (EI) 162 (M–H)$^+$
$^1$H NMR (CDCl$_3$) 8.55–8.35(2H, m); 7.53(1H, d); 7.25–7.15(1H, m); 6.0–5.8(1H, m); 5.35–5.05(2H, m); 4.2–4.05(1H, m); 2.85–2.6(2H, m); 2.0–1.65(3H, m).

b) 1-(Benzo-1,4-dioxan-6-yl)-5-(pyridin-3-yl)-3-pentanone and (±)-trans-1-(Benzo-1,4-dioxan-6-yl)-5-(pyridin-3-yl)-pent-1-en-3-ol A mixture of palladium(II) acetate (0.112 g), tri-o-tolylphosphine (0.304 g), 3,4-ethylenedioxybromobenzene (1.075 g) and (±)-5-(pyridin-3-yl)-1-penten-3-ol (0.815 g, Example 1a)) in triethylamine (10 ml) in acetonitrile (30 ml) was heated at 80° C. for 3 hours and 30 minutes. The mixture was cooled to room temperature and filtered through Celite® and the filtrate concentrated under reduced pressure. The residue was redissolved in ethyl acetate and the solution washed with water then dried over anhydrous magnesium sulfate. The solution was then filtered and concentrated under reduced pressure. The residue was purified by column chromatography over silica eluting with hexane:acetone (3:1) then (2:1) to give firstly 1-(benzo-1,4-dioxan-6-yl)-5-(pyridin-3-yl)-3-pentanone as an oil (0.812 g) and secondly (±)-trans-1-(benzo-1,4-dioxan-6-yl)-5-(pyridin-3-yl)-pent-1-en-3-ol as an oil (0.252 g).

Ketone
MS (EI) 297 (M)$^+$
1H NMR (CDCl$_3$) 8.43(2H, d); 7.47(1H, d); 7.19(1H, dd); 6.76(1H, d); 6.66(1H, s); 6.61(1H, dd); 4.23(4H, s); 2.88 (2H, t); 2.85–2.75(2H, m); 2.75–2.65(4H, m).

Alcohol
MS (EI) 297 (M)$^+$
1H NMR (CDCl$_3$) 8.48(1H, s); 8.44(1H, d); 7.53(1H, d); 7.21(1H, dd); 6.95–6.75(3H, m); 6.46(1H, d); 6.08(1H, dd); 4.26(5H, m); 2.8–2.7(2H, m); 2.05–1.85(2H, m).

c) (±)-1-(2,3-Dihydro-benzo[1,4]dioxin-6-yl)-5-pyridin-3-yl-pentan-3-ol.

A mixture of 1-(benzo-1,4-dioxan-6-yl)-5-(pyridin-3-yl)-3-pentanone (0.81 g, from part b) and (±)-trans-1-(benzo-1,4-dioxan-6-yl)-5-(pyridin-3-yl)-pent-1-en-3-ol (0.25 g, Example 1b)) and sodium borohydride (0.156 g) were dissolved in ethanol (20 ml) and stirred for 2 hours at room temperature. The solution was concentrated under reduced pressure and then 2M hydrochloric acid (2 ml) was added. Water was added to the solution and the mixture neutralised by the addition of a saturated aqueous solution of sodium bicarbonate. The organic component was extracted with ethyl acetate and the combined extracts dried over anhydrous magnesium sulfate, filtered and concentrated under reduced pressure. The residue was dissolved in ethanol (20 ml) and was hydrogenated at 1 atmosphere pressure for 4 hours using 10% palladium on carbon (0.1 g) as catalyst. The reaction mixture was filtered through Celite® and the filtrate concentrated under reduced pressure. The residue was purified by column chromatography over silica eluting with hexane:acetone (2:1) to give the title compound as an oil (0.63 g).

MS (EI) 299 (M)$^+$
$^1$H NMR (CDCl$_3$) 8.5–8.4(2H, m); 7.50(1H, d); 7.20(1H, dd); 6.77(1H, d); 6.69(1H, d); 6.65(1H, dd); 4.24(4H, s); 3.7–3.6(1H, m); 2.85–2.5(4H, m); 1.85–1.7(4H, m).

EXAMPLE 2
(±)-1-(2,3-Dihydro-benzo[1,4]dioxin-6-yloxy)-4-pyridin-3-yl-butan-2-ol

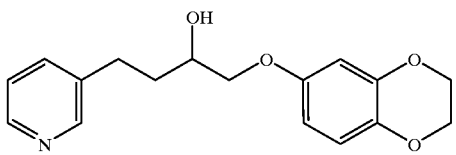

a) (±)-α-(Chloromethyl)-3-pyridinepropanol

A solution of 3-picoline (19.4 ml) in dry tetrahydrofuran was added to a solution of lithium diisopropylamide in tetrahydrofuran at −10° C. under a nitrogen atmosphere (prepared by adding n-butyllithium (2.5 M in hexanes, 80 ml) to a solution of diisopropylamine (28 ml) in dry tetrahydrofuran (80 ml)). The resulting bright yellow suspension was stirred at −10° C. for 1 hour, and was then transferred via a double ended needle to a solution of (±)-epichlorohydrin (15.6 ml) in tetrahydrofuran (80 ml) at −10° C. under nitrogen. After addition the mixture was stirred and allowed to warm up to room temperature over 1 hour. The reaction was quenched by addition of a solution of saturated aqueous ammonium chloride (200 ml) and was then made acidic by addition of hydrochloric acid (2 M) whilst keeping the temperature below 20° C. The mixture was stirred at ambient temperature for 1 hour, and then re-basified by the addition of solid sodium bicarbonate. The product was extracted with ethyl acetate, the combined extracts washed with brine, dried over anhydrous magnesium sulfate, filtered and concentrated under reduced pressure. The residue was purified by column chromatography over silica eluting with dichloromethane:ethanol (95:5) to give the sub-title compound as an oil (9.66 g).

MS(EI) 185 (M)+

$^1$H NMR (DMSO) 8.43(1H, d); 8.4(1H, dd); 7.63(1H, dd); 7.35–7.27(1H, m); 5.22(1H, d); 3.65–3.5(3H, m); 2.8–2.55(2H, m); 1.85–1.6(2H, m).

b) (±)-1-(2,3-Dihydro-benzo[1,4]dioxin-6-yloxy)-4-pyridin-3-yl-butan-2-ol

A solution of benzo-1,4-dioxan-6-ol (0.15 g; *Tetrahedron*, 1995, 3197) in ethanol (20 ml) at room temperature was treated with a solution of sodium hydroxide (0.044 g) in water (5 ml) and was then heated at reflux. A solution of (±)-α-(chloromethyl)-3-pyridinepropanol (1.0 g) in ethanol (5 ml) was added dropwise to the latter and the resulting mixture heated at reflux for 1 hour. The reaction mixture was cooled and then water was added. The organic component was extracted with dichloromethane, the combined extracts dried over anhydrous magnesium sulfate, filtered and concentrated under reduced pressure. The residue was purified by column chromatography over silica eluting with ethyl acetate to give an oil (0.100 g).

MS (EI) 301 (M)+

$^1$H NMR (CDCl$_3$) 8.55–8.45(2H, m); 7.6–7.55(1H, m); 7.3–7.2(1H, m); 6.8–6.75(1H, m); 7.5–7.35(2H, m); 4.3–4.2 (4H, bs); 4.0–3.7(3H, m); 3.0–2.7(2H, m); 2.45(1H, bs); 1.95–1.8(2H, m).

EXAMPLE 3

(±)-1-([9H]-Fluoren-2-yloxy)-4-pyridin-3-yl-butan-2-ol

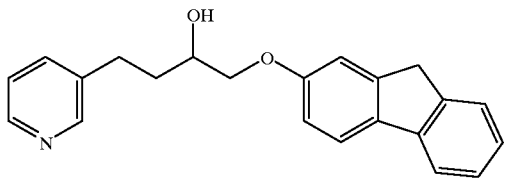

Prepared according to the method described in Example 2b) from 2-hydroxyfluorene (1.96 g), ethanol (30 ml), sodium hydroxide (0.43 g), water (10 ml) and (±)-α-(chloromethyl)-3-pyridinepropanol (1.0 g, from Example 2a) to give the title compound as a beige solid (0.406 g).

m.p. 115–117° C.

MS (EI) 331 (M)+

$^1$H NMR (DMSO) 8.45(1H, s); 8.40(1H, d); 7.77(2H, d); 7.65(1H, d); 7.53(1H, d); 7.37–7.29(2H, m); 7.25–7.15(2H, m); 6.95(1H, d); 5.08(1H, d); 3.95(2H, d); 3.85(2H, s); 3.83–3.75(1H, m); 2.88–2.64(2H, m); 1.93–1.67(2H, m).

EXAMPLE 4

(±)-1-(Dibenzofuran-3-yloxy)-4-pyridin-3-yl-butan-2-ol

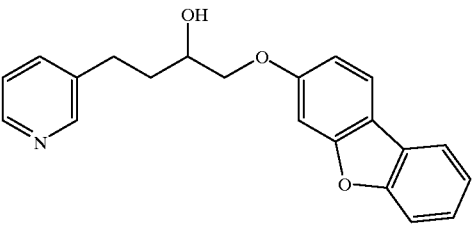

Prepared according to the method described in Example 2b) from 2-hydroxydibenzofuran (0.80 g), ethanol (15 ml), sodium hydroxide (0.21 g), water (2.5 ml) and (±)-α-(chloromethyl)-3-pyridinepropanol (0.70 g, from Example 2a) to give a crude product. This was purified by column chromatography over silica eluting with ethyl acetate to give material that was further purified by normal phase HPLC eluting with dichloromethane:tetrahydrofuran (4:1) to give the title compound as a solid (0.46 g).

m.p. 119–120° C.

MS (APCI) 334 (M+H)+

$^1$H NMR (DMSO) 8.48(1H, d); 8.40(1H, dd); 8.13(1H, d); 7.72(1H, d); 7.70–7.65(2H, m); 7.59(1H, d); 7.51(1H, td); 7.41–7.29(2H, m); 7.10(1H, dd); 5.10(1H, d); 4.00(2H, d); 3.9–3.75(1H, m); 2.9–2.65(2H, m); 1.95–1.65(2H, m).

EXAMPLE 5

(2R)-1-[4-(5-Chloro-thiophen-2-yl)-phenoxy]-4-pyridin-3-yl-butan-2-ol, trifluoroacetic acid salt

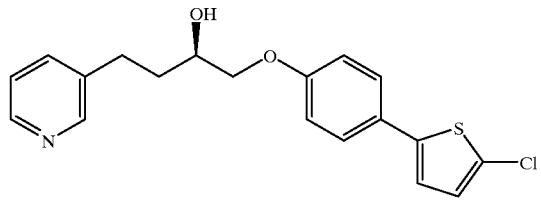

a) (2R,3E/Z)-4-(Pyridin-3-yl)-1,2-O-isopropylidenebut-3-en-1,2-diol

A solution of n-butyllithium (2.5 M in hexanes; 100.8 ml) was added dropwise to a stirred suspension of pyridin-3-ylmethyltriphenylphosphonium chloride hydrochloride (53.39 g, *J. Med. Chem.* 1986, 29, 1461) in tetrahydrofuran (50 ml) at −40° C. The resulting mixture was stirred at room temperature for 30 minutes and was then cooled to −70° C. A solution of 2,3-O-(S)-isopropylidene-l-glyceraldehyde (15.2 g) (prepared by the method of *Organic Synthesis* (1995) 72, 1) in tetrahydrofuran (10 ml) was added. The resulting mixture was stirred and allowed to reach room temperature over 3 hours. The mixture was poured into brine (500 ml) and extracted into ethyl acetate. The combined extracts were dried over anhydrous magnesium sulfate, filtered and concentrated under reduced pressure. The residue was purified by column chromatography over silica eluting with diethyl ether to give the sub-title compound as an oil (21.2 g).

MS (EI) 205 (M)+

$^1$H NMR (CDCl$_3$) major Z-diastereomer 8.53(2H, d); 7.61(1H, dt); 7.29(1H, dd); 6.67(1H, d); 5.85(1H, dd); 4.83(1H, q); 4.16(1H, t); 3.71(1H, t); 1.49(3H, s); 1.39(3H, s).

b) (2R)-4-(Pyridin-3-yl)-1,2-O-isopropylidenebutane-1,2-diol

A solution of (2R,3E/Z)-4-(pyridin-3-yl)-1,2-O-isopropylidenebut-3-en-1,2-diol (21.2 g, Example 5a)) in ethyl acetate (200 ml) was hydrogenated for 2 hours at 3 atmospheres pressure using 10% palladium on carbon (0.5 g) as catalyst. The reaction was filtered through Celite® and the residue washed with ethyl acetate. The combined filtrate and washings were concentrated under reduced pressure and the residue obtained purified by column chromatography over silica eluting with diethyl ether to give the sub-title compound as an oil (20.5 g).

MS (ESI) 208 (M+H)$^+$ $^1$H NMR (CDCl$_3$) 8.48–8.45(2H, m); 7.52(1H, dt); 7.23 (1H, dd); 4.10(1H, quintet); 4.04(1H, t); 3.55(1H, t); 2.84–2.64(2H, m); 1.94–1.80(2H, m); 1.44(3H, s), 1.36(3H, s).

c) (2R)-4-(Pyridin-3-yl)-1,2-butanediol (2R)-4-(Pyridin-3-yl)-1,2-O-isopropylidenebutane-1,2-diol (20.4 g, Example 5b)) was dissolved in 2M hydrochloric acid (100 ml) and was stirred for 40 minutes. The mixture was neutralised with saturated aqueous sodium hydrogencarbonate solution and was concentrated under reduced pressure. The residue obtained was triturated with ethyl acetate and filtered. The residue was washed with ethyl acetate and the combined organic extracts were dried over anhydrous magnesium sulfate, filtered and concentrated under reduced pressure. The residue obtained was purified by column chromatography over silica eluting with ethyl acetate:methanol (9:1) to give the sub-title compound as an oil (16.4 g).

MS (APCI) 168 (M+H)$^+$ $^1$H NMR (CDCl$_3$) 8.44–8.40(2H, m); 7.54(1H, d); 7.22 (1H, dd); 3.73–3.67(1H, m); 3.65(1H, dd); 3.48(1H, dd); 2.90–2.70(2H, m); 2.87–2.68(2H, m); 1.84–1.67(2H, m).

d) (2R)-2-(tert-Butyldimethylsilyloxy)-4-(pyridin-3-yl)-1-butyl para-toluenesulfonate (2R)-4-(Pyridin-3-yl)-1,2-butanediol (10.00 g, Example 5c)) was dissolved in pyridine (60 ml) and dichloromethane (60 ml) and solid para-toluenesulfonyl chloride (17.2 g) added at 0° C. The resulting mixture was stirred at room temperature for 8 hours and then concentrated under reduced pressure. The residue was partitioned between ethyl acetate and a solution of saturated aqueous sodium hydrogencarbonate. The organic extract was dried over anhydrous magnesium sulfate, filtered and concentrated under reduced pressure. The resulting oil was dissolved in dimethylformamide (50 ml) and imidazole (10.5 g) followed by tert-butyldimethylsilyl chloride (6.8 g) were added. The mixture was stirred for 20 hours and was then poured into water (200 ml). The mixture was extracted with ethyl acetate and the combined organic extracts dried over anhydrous magnesium sulfate, filtered and concentrated under reduced pressure. The residue obtained was purified by column chromatography over silica eluting with diethyl ether to give the sub-title compound as an oil (14.08 g).

MS (APCI) 436 (M+H)$^+$ $^1$H NMR (CDCl$_3$) 8.40 (1H, d); 8.35 (1H, s); 7.73 (2H, d); 7.40 (1H, d); 7.29 (2H, d); 7.16 (1H, dd); 3.90–3.83 (1H, m); 3.86 (2H, s); 2.64–2.48 (2H, m); 2.40 (3H, s); 1.82–1.65 (2H, m); 0.82 (9H, s); 0.01 (3H, s); −0.19 (3H, s).

e) (2R)-1-(4-Bromophenoxy)-4-(pyridin-3-yl)-2-butanol

Solid 4-bromophenol (2.08 g) was added to a stirred suspension of sodium hydride (60%, 0.48 g) in dimethylformamide (30 ml) and the resulting solution stirred for 30 minutes. (2R)-2-(tert-butyldimethylsilyloxy)-4-(pyridin-3-yl)-1-butyl para-toluenesulfonate (4.35 g, Example 5d)) was added and the mixture stirred at 60° C. for 2 hours. After cooling the mixture was poured into water (50 ml) and extracted with ethyl acetate. The combined organic extracts were dried over anhydrous magnesium sulfate, filtered and concentrated under reduced pressure. The residue obtained was dissolved in acetonitrile (20 ml) and hydrofluoric acid (40% in water; 5 ml, CAUTION) was added. The mixture was stirred for 1 hour and then poured into a solution of saturated aqueous sodium hydrogencarbonate. The mixture was extracted with ethyl acetate and the combined organic extracts were dried over anhydrous magnesium sulfate, filtered and concentrated under reduced pressure. The residue obtained was purified by column chromatography over silica eluting with acetone:hexane (1:1) to give the sub-title compound as a solid (2.65 g).

m.p. 65–66° C.

MS (APCI) 323 (M+H)$^+$ $^1$H NMR (CDCl$_3$) 8.53(1H, d); 8.4(1H, d); 7.58(1H, dt); 7.38(2H, d); 7.24(1H, dd); 6.80(2H, d); 4.2–3.94(1H, m); 3.92(1H, dd); 3.82(1H, dd); 2.9–2.84(1H, m); 2.82–2.72 (1H, m); 2.46(1H, br); 1.96–1.80(2H, m).

f) (2R)-1-[4-(5-Chloro-thiophen-2-yl)-phenoxy]-4-pyridin-3-yl-butan-2-ol, trifluoroacetic acid salt Aqueous sodium carbonate solution (2M, 0.7 ml) was added to a solution (2R)-1-(4-bromophenoxy)-4-(pyridin-3-yl)-2-butanol (0.197 g, Example 5e)), 5-chlorothiophene-2-boronic acid (0.126 g) and tetrakis(triphenylphosphine) palladium(0) (0.018 g) in ethanol (0.8 ml) and toluene (3 ml). The mixture was heated at reflux under a nitrogen atmosphere for 2 hours and was then cooled to room temperature, diluted with water and extracted with ethyl acetate. The combined organic extracts were dried over anhydrous magnesium sulfate, filtered and concentrated under reduced pressure. The residue was purified by column chromatography over silica eluting with dichloromethane:methanol (19:1) to give the free base of the title compound (0.18 g) as a solid. This was further purified by preparative reverse phase HPLC on a μBondapak column eluting with aqueous trifluoroacetic acid (0.1%) and methanol. The solution was concentrated under reduced pressure to remove methanol and a solution of saturated aqueous sodium bicarbonate solution was added. The mixture was extracted with ethyl acetate and the combined extracts dried over anhydrous magnesium sulphate, filtered and concentrated under reduced pressure. The residue was triturated with ether to give the title compound as a solid (0.048 g).

m.p. 94–98° C.

MS (APCI) 360.2/362.2 (M+H)$^+$ $^1$H NMR (DMSO) 8.49 (1H, d); 8.42 (1H, dd); 7.57 (1H, dt); 7.41 (2H, d); 7.23 (1H, dd); 6.98 (1H, d); 6.92 (2H, d); 6.87 (1H, d); 4.58 (1H, br); 3.98–3.92 (3H, m); 2.98–2.84 (1H, m); 2.81–2.71 (1H, m); 1.97–1.84 (2H, m).

EXAMPLE 6

(±)-1-(Benzofuran-6-yloxy)-4-pyridin-3-yl-butan-2-ol.

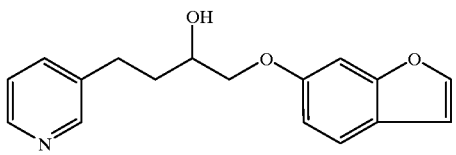

(±)-α-(Chloromethyl)-3-pyridinepropanol (0.339 g, Example 2a)) was dissolved in anhydrous N,N-dimethylformamide (5 ml) and added to a suspension of 6-hydroxybenzofuran (0.245 g, *Bull. Soc. Chim. Fr.*, 1973, 2355) and cesium carbonate (0.596 g) in anhydrous N,N-dimethylformamide (5 ml) which had been heated previously for one hour at 120° C. The mixture was then heated at 120° C. for 7 hours before being cooled to room temperature. The mixture was then poured into water and extracted with ethyl acetate. The combined organic extracts were washed with brine, dried over anhydrous magnesium sulfate, filtered and concentrated under reduced pressure. The residue was purified by column chromatography over silica eluting with dichloromethane:ethanol (19:1) and recrystallised from ethyl acetate:hexane to give the title compound (0.129 g).

m.p. 102–103° C.

MS (APCI) 284 (M+H)$^+$ $^1$H NMR (DMSO); 8.46(1H, d); 8.40(1H, d); 7.85(1H, d); 7.60(1H, d); 7.48(1H, d); 7.30(1H, m); 7.10(1H, d); 6.90 (2H, m); 5.00 (1H, d); 3.90(2H, d); 3.79(1H, m); 2.73(2H, m); 1.74(2H, m).

EXAMPLE 7

(2R)-5-[4-(2-Hydroxy-4-pyridin-3-yl-butoxy)-phenyl]-1,3-dimethyl-1#H!-pyrimidine-2,4-dione, oxalic acid salt

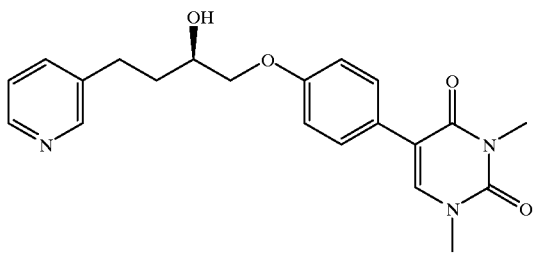

a) (2R)-2-(4-Bromophenoxy)-3-tert-butyldimethylsilanyloxy-4-pyridin-3-ylbutane tert-Butyldimethylsilyl chloride (17.73 g), followed by imidazole (7.99 g) were added to a solution of (2R)-1-(4-bromophenoxy)-4-pyridin-3-ylbutan-2-ol (18.91 g, Example 5e)) in anhydrous dichloromethane (500 ml), under an inert atmosphere. The mixture was stirred overnight at room temperature. The precipitate was filtered off and the filtrate was concentrated under reduced pressure. The residue was purified by column chromatography over silica eluting with dichloromethane:ethyl acetate (5:1) to give the sub-title compound as an oil (25.55 g).

MS (APCI) 438 (M+2)$^+$ $^1$H NMR (DMSO) 8.48(1H, d); 8.44(1H, dd); 7.67(1H, d); 7.49(2H, d); 7.36(1H, dd); 6.94(2H, d); 4.08–4.01(2H, m); 3.93–3.89(1H, m); 2.77–2.73(2H, m); 2.02–1.85(2H, m); 0.91(9H, s); 0.13(3H, s); 0.9(3H, s).

b) (2R)-4-[2-(tert-Butyldimethylsilanyloxy)-4-pyridin-3-yl-butoxy]benzeneboronic acid A solution of tert-butyllithium (9.7 ml, 1.7M in pentane) was added over a 1 hour period to a solution of (2R)-2-(4-bromophenoxy)-3-tert-butyldimethylsilyloxy-4-(pyridin-3-yl)butane (6.0 g, Example 7a)) and tri-isopropylborate (4.9 ml) in tetrahydrofuran (150 ml) at −78° C. The resulting solution was stirred at −78° C. for 2 hours and was then quenched by the addition of a saturated solution of ammonium chloride in water (50 ml). The mixture was poured into water (50 ml) and extracted into ethyl acetate (2×50 ml). The combined extracts were dried over anhydrous magnesium sulfate, filtered and concentrated. The residue was purified by chromatography on silica eluting with ethyl acetate and then ethyl acetate:methanol (5:1) to afford the sub-title compound as a foam (3.88 g).

MS (APCI) 402 (M+H)$^+$ $^1$H NMR (CDCl$_3$) 8.62–8.57(2H, m); 7.96(2H, d); 7.62–7.59(1H, m); 7.31–7.27(1H, m); 6.88 (2H, d); 4.16–4.08(1H, m); 3.96–3.81(2H, m); 2.85–2.71(2H, m); 1.99–1.85(2H, m); 0.91 (9H, s); 0.10 (6H, s).

c) (2R)-5-[4-(2-Hydroxy-4-pyridin-3-yl-butoxy)-phenyl]-1,3-dimethyl-1#H!-pyrimidine-2,4-dione, oxalic acid salt Toluene (10 ml), 2M aqueous sodium carbonate (1 ml), (2R)-4-[2-(tert-butyldimethylsilanyloxy)-4-pyridin-3-yl-butoxy]benzeneboronic acid. (Example 7b), 0.526 g), and tetrakis(triphenylphosphine)palladium(0) (0.03 g) were added to a solution of 5-bromo-1,3-dimethyluracil (0.438 g) in ethanol (4 ml). The mixture was heated at 110° C. for 4 hours. The mixture was cooled to room temperature and made acid by addition of 2M aqueous hydrochloric acid solution (5 ml). The mixture was extracted with diethyl ether (20 ml). The aqueous layer was basified by addition of aqueous sodium hydroxide (2M), and extracted with ethyl acetate (3×50 ml). The combined extracts were dried over anhydrous magnesium sulfate, filtered and concentrated under reduced pressure. The residue was purified by column chromatography over silica eluting dichloromethane:acetone (1:2) to give an oil, which was converted to the oxalate salt upon treatment with oxalic acid (excess) in ether to give the title compound as a solid (0.407 g).

m.p. 152–154° C.

MS (APCI) 382 ((M-oxalic acid)+H)$^+$ $^1$H NMR (DMSO) 8.50(1H, d); 8.44(1H, dd); 7.95(1H, s); 7.71–7.67(1H, m); 7.52(2H, d); 7.37–7.33(1H, m); 6.98(2H, d); 4.07(2H, q); 3.90–3.81(1H, m); 3.42(3H, s); 3.28(3H, s); 2.93–2.65(2H, m); 1.95–1.67(2H, m).

EXAMPLE 8

(2R)-1-[4-(2,4-Dimethoxy-pyrimidin-5-yl)-phenoxy]-4-pyridin-3-yl-butan-2-ol, oxalic acid salt

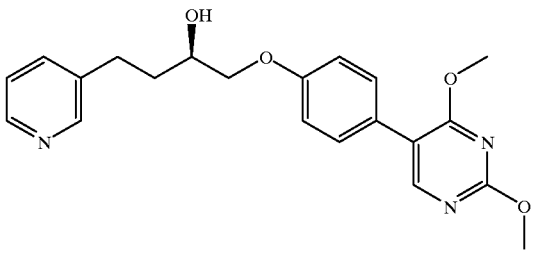

Prepared according to the method described in Example 7c) from 5-bromo-2,4-dimethoxypyrimidine (0.438 g), ethanol (4 ml), toluene (10 ml), 2M aqueous sodium carbonate (1 ml), (2R)-4-[2-(tert-butyldimethylsilanyloxy)-1-methyl-4-pyridin-3-yl-butoxy]benzeneboronic acid (Example 7b), 0.526 g), and tetrakis(triphenylphosphine)palladium(0) (0.03 g). After work up, the residue was purified by column chromatography over silica eluting ethyl acetate to give an oil, which was converted to the oxalate salt upon treatment with oxalic acid (excess) in ether to give the title compound as a solid (0.526 g).

m.p. 150–153° C.

MS (APCI) 382 ((M-oxalic acid)+H)$^+$ $^1$H NMR (DMSO) 8.48(1H, d); 8.42(1H, d); 8.32(1H, s); 7.70(1H, d); 7.43 (2H, d); 7.37–7.33(1H, m); 6.99(2H, d); 3.93(6H, s); 3.92(2H, d); 3.81–3.75(1H, m); 2.85–2.64(2H, m); 1.88–1.70(2H, m).

EXAMPLE 9

(2R)-5-[4-(2-Hydroxy-4-pyridin-3-yl-butoxy)-phenyl]-1H-pyrimidine-2,4-dione

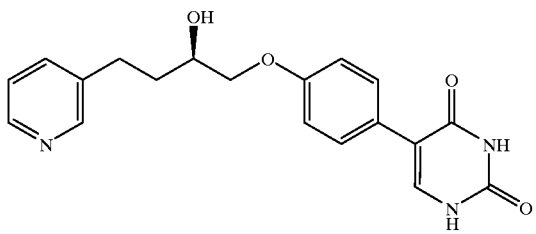

Aqueous hydrochloric acid solution (5M, 3 ml) was added to (2R)-1-(5-[2,4-dimethoxypyrimidyl]phenyl-4-yloxy)-4-(pyridin-3-yl)-2-butanol (Example 8, 0.237 g) dissolved in methanol (3 ml). The mixture was heated at reflux for 22 hours. The mixture was cooled to room temperature and neutralised by addition of 2M aqueous sodium hydroxide solution. It was extracted with ethyl acetate (3×10 ml) and the combined extracts dried over anhydrous magnesium sulfate, filtered and concentrated under reduced pressure. The residue was purified by column chromatography over silica eluting dichloromethane:methanol (95:5) to give a solid, which was recrystallised in a methanol:iso-hexane mixture to give the title compound as a solid (0.033 g).

m.p. 245–246° C.

MS (APCI) 354 (M+H)$^+$ $^1$H NMR (DMSO) 11.18(1H, bs); 11.02(1H, bs); 8.45(1H, d); 8.39(1H, dd); 7.65(1H, d); 7.52(1H, s); 7.44(2H, d); 7.33–7.28(1H, m); 6.91(2H, d); 5.05(1H, d); 3.88(2H, d); 3.79–3.75(1H, m); 2.78–2.66(2H, m); 1.85–1.68(2H, m).

EXAMPLE 10

(2R)-4-[4-(2-Hydroxy-4-pyridin-3-yl-butoxy)phenyl]-1H-pyridin-2-one

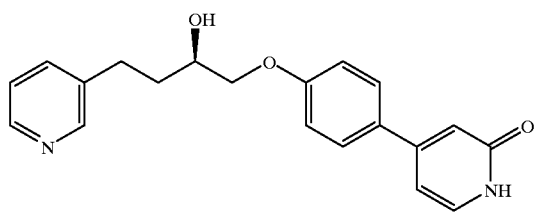

Prepared according to the method described in Example 7c) from 4-bromo-pyridin-2-one (0.125 g), ethanol (4 ml), toluene (10 ml), 2M aqueous sodium carbonate (0.36 ml), (1S,2R)-4-[2-(tert-butyldimethylsilanyloxy)-1-methyl-4-pyridin-3-yl-butoxy]benzeneboronic acid (Example 7b), 0.292 g), and tetrakis(triphenylphosphine)palladium(0) (0.03 g). After work up, the residue was purified by column chromatography over silica eluting dichloromethane:methanol (95:5) to give a white solid which was recrystallised in an ethyl acetate:iso-hexane mixture to give the title compound as a solid (0.058 g).

m.p. 138–141° C.

MS (APCI) 337 (M+H)$^+$ $^1$H NMR (DMSO) 8.5(1H, d); 8.44(1H, dd); 7.58(1H, d); 7.53(2H, d); 7.31(1H, d); 7.23(1H, dd); 6.98(2H, d); 6.68(1H, d); 6.45(1H, dd); 3.98(2H, bs); 3.83(1H, bs); 2.97–2.72(2H, m); 1.91(2H, q).

EXAMPLE 11

(2R)-5-[4-(2-Hydroxy-4-pyridin-3-yl-butoxy)-phenyl]-1H-pyridin-2-one, oxalic acid salt

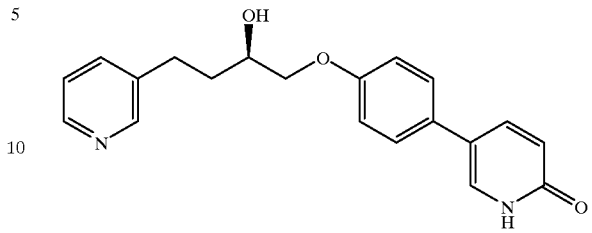

Prepared according to the method described in Example 7c) from 5-iodo-pyridin-2-one (0.250 g), ethanol (4 ml), toluene (10 ml), 2M aqueous sodium carbonate (0.6 ml), (2R)-4-[2-(tert-butyldimethylsilanyloxy)-4-pyridin-3-yl-butoxy]benzeneboronic acid (Example 7b), 0.378 g), and tetrakis(triphenylphosphine)palladium(0) (0.03 g). After work up, the residue was purified by column chromatography over silica eluting dichloromethane:methanol (95:5) to give an oil which was converted to the oxalate salt upon treatment with oxalic acid (excess) in ether to give the title compound as a solid (0.094 g).

m.p. 98–101° C.

MS (APCI) 337 ((M-oxalic acid)+H)$^+$ $^1$H NMR (DMSO) 8.49(1H, s); 8.43(1H, d); 7.79–7.72 (2H, m); 7.59(1H, d); 7.45(2H, d); 7.40–7.35(1H, m); 6.96 (2H, d); 6.40(1H, d); 3.89(2H,d); 3.82–3.70(1H, m); 3.92–3.65(2H, m); 2.93–2.64(2H, m).

EXAMPLE 12

(2R)-4-[4-(2-Hydroxy-4-pyridin-3-yl-butoxy)-phenyl]-1-methyl-1H-pyridin-2-one

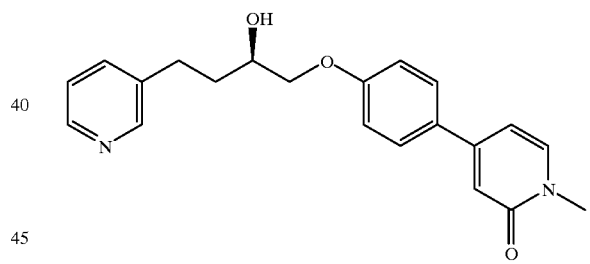

a) 4Bromo-1-methylpyridin-2-one

Some freshly cut sodium metal (0.016 g) was added to dry ethanol (42 ml). The solution was stirred at room temperature for half an hour before 4-bromopyridin-2-one (0.125 g) was added. After stirring overnight the solvents were evaporated under reduced pressure. The mixture was redissolved in dimethylformamide (25 ml) and methyl iodide (0.09 ml) was added to the solution. The mixture was stirred at room temperature overnight. Water (10 ml) was added and the reaction mixture was extracted with ethyl acetate (3×50 ml). The combined extracts were dried over anhydrous magnesium sulfate, filtered and concentrated under reduced pressure to give the sub-title compound as a brown solid (0.128 g).

m.p. 73–75° C.

MS (APCI) 188 (M+H)$^+$ $^1$H NMR (DMSO) 7.68(1H, d); 6.70(1H, d); 6.44(1H, dd); 3.37(3H, s).

b) (2R)-4-[4-(2-Hydroxy-4-pyridin-3-yl-butoxy)-phenyl]-1-methyl-1H-pyridin-2-one.

Prepared according to the method described in Example 7c) from 4-bromo-N-methylpyridin-2-one (Example 12a), 0.128 g), ethanol (4 ml), toluene (10 ml), 2M aqueous sodium carbonate (0.34 ml), (2R)-4-[2-(tert-butyldimethylsilanyloxy)-4-pyridin-3 -ylbutoxy]benzeneboronic acid (Example 7c), 0.273 g), and tetrakis(triphenylphosphine)palladium(0) (0.03 g). After work up, the residue was purified by column chromatography over silica eluting dichloromethane:methanol (95:5) to give the title compound as a solid (0.116 g).

m.p. 114–115° C.

MS (APCI) 351 (M+H)+

$^1$H NMR (DMSO) 8.46(1H, s); 8.40(1H, d); 7.72(1H, d); 7.68–7.64(3H, m); 7.31(1H, dd); 7.02(2H, d); 6.61(1H, d); 6.55(1H, dd); 5.07(1H, bs); 3.94(2H, d); 3.78(1H, bs); 3.42(3H, s); 2.86–2.62(2H, m); 1.92–1.67(2H, m).

EXAMPLE 13

(2R)-5-[4-(2-Hydroxy-4-pyridin-3-yl-butoxy)phenyl]-1-methyl-1H-pyridin-2-one

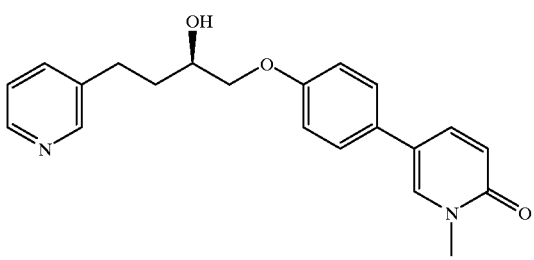

a) 5-Iodo-1-methylpyridin-2-one

Prepared according to the method described in Example 12a) from sodium metal (0.026 g), ethanol (66 ml), 5-iodopyridin-2-one (0.250 g), dimethylformamide (25 ml) and methyl iodide (0.141 ml) to give, on workup, the sub-title compound as an oil (0.252 g).

MS (APCI) 236 (M+H)+

$^1$H NMR (DMSO) 8.02(1H, d); 7.54(1H, dd); 6.24(1H, d); 3.38(1H, s).

b) (2R)-5-[4-(2-Hydroxy-4-pyridin-3-yl-butoxy)phenyl]-1-methyl-1H-pyridin-2-one

Prepared according to the method described in Example 7c) from 5-iodo-N-methylpyridin-2-one (Example 13a), 0.276 g), ethanol (4 ml), toluene (10 ml), 2M aqueous sodium carbonate (0.58 ml), (2R)-4-[2-(tert-butyldimethylsilanyloxy)-4-pyridin-3-yl-butoxy]benzeneboronic acid (Example 7b), 0.471 g), and tetrakis(triphenylphosphine)palladium(0) (0.03 g). After work up, the residue was purified by column chromatography over silica eluting dichloromethane:methanol (95:5) to give the title compound as a foam (0.191 g).

MS (APCI) 351 (M+H)+

$^1$H NMR (DMSO) 8.48(1H, s); 8.41(1H, d); 8.02(1H, d); 7.76(1H, dd); 7.69(1H, d); 7.47(2H, d); 7.34(1H, dd); 6.98 (2H, d); 6.45(1H, d); 3.90(2H, d); 3.80–3.75(1H, m); 3.49 (3H, s); 2.84–2.63(2H, m); 1.86–1.65(2H, m).

EXAMPLE 14

(2R)-1-(4-[1,3,4]-Oxadiazol-2-ylphenoxy)-4-pyridin-3-yl-butan-2-ol.

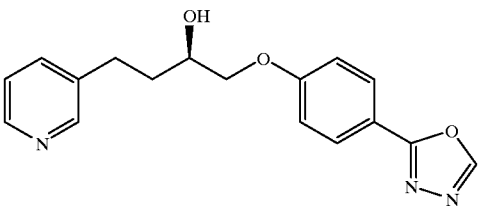

a) (4R)-4-[2-(Pyridin-3-yl)ethyl]-1,3-dioxin-2-one

A solution of (2R)-4-(Pyridin-3-yl)-1,2-butanediol (0.42 g, Example 5c)) and 1,1'-carbonyldi-imidazole (0.49 g) in chloroform (15 ml) was heated at reflux for 20 minutes. The reaction was cooled and concentrated under reduced pressure. The residue was purified by column chromatography over silica eluting with methanol:dichloromethane (1:19) to give the sub-title compound as an oil (0.35 g).

MS (APCI) 194 (M+H)+

$^1$H NMR (CDCl$_3$) 8.52–8.49(2H, m); 7.53(1H, d); 7.26 (1H, dd); 4.73–4.66(1H, m); 4.54 (1H, dd); 4.09 (1H, dd); 2.94–2.88 (1H, m); 2.86–2.72 (1H, m); 2.17–2.09 (1H, m); 2.02–1.97 (1H, m).

b) (2R)-1-(4-[1,3,4]-Oxadiazol-2-ylphenoxy)-4-pyridin-3-yl-butan-2-ol.

Cesium carbonate (0.72 g) and 4-(1,3,4)-oxadiazol-2-yl-phenol (0.54 g) were added to a solution of (4R)-4-[2-(pyridin-3-yl)ethyl]-1,3-dioxin-2-one (1.20 g, Example 14a)) in dry dimethylformamide (75 ml) and heated at 90° C. for 14 hours. After cooling, the reaction mixture was poured into water (50 ml) and extracted three times with ethyl acetate. The combined organic phases were extracted twice with 2M hydrochloric acid. The combined aqueous extracts were basified by dropwise addition of 2M aqueous sodium hydroxide and the aqueous solution was then extracted three times with ethyl acetate. The organic extracts were combined and dried over anhydrous magnesium sulfate, filtered and concentrated under reduced pressure. The residue was purified by normal phase HPLC eluting with 0 to 25% ethanol in dichloromethane to give the title compound as a solid (0.19 g).

m.p. 130–133° C.

MS (APCI) 312 (M+H)+

$^1$H NMR (DMSO) 9.27(1H, s); 8.47(1H, m); 8.40(1H, dd); 7.95(2H, m); 7.66(1H, m); 7.32(1H, dd); 7.13(2H, m); 5.10(1H, d); 3.99(2H, m); 3.81(1H, m); 2.75(2H, m); 1.79 (2H, m).

EXAMPLE 15

(2S,3R)-2-(4-(2,4-Dimethoxypyrimidin-5-yl)phenoxy)-5-pyridin-3-yl-pentan-3-ol.

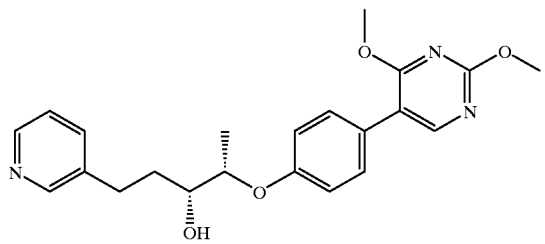

a) (2S)-2-(4-Bromophenoxy)propanoic acid, ethyl ester

Diethylazodicarboxylate (6.74 ml) in dry tetrahydrofuran (25 ml) was added dropwise over 30 minutes to a stirred solution of triphenylphosphine (13.11 g), (R)-(+)-ethyl lactate (5.67 ml) and 4-bromophenol (8.65 g) in dry tetrahydrofuran (125 ml). The resulting solution was stirred at room temperature for 18 hours then concentrated under reduced pressure. A mixture of isohexane:ether (9:1) (200 ml) was added to the residue and the mixture was stirred at room temperature for 30 minutes. The solution was filtered and the filtrate concentrated under reduced pressure. The residue was purified by column chromatography over silica eluting with isohexane:dichloromethane (2:3) to give the sub-title compound as an oil (12.2 g).

$^1$H NMR (CDCl$_3$) 7.36(2H, d); 6.75(2H, d); 4.69(1H, q); 4.20(2H, q); 1.61(3H, d); 1.25(3H, t).

b) (2S)-2-(4-Bromophenoxy)-1-propanol

Sodium borohydride (1.15 g) was added to a solution of (2S)-2-(4-bromophenoxy)propanoic acid, ethyl ester (7.5 g, Example 15a)) in ethanol (20 ml) at 5° C. The resulting solution was allowed to warm to room temperature and was stirred for 10 hours before being concentrated under reduced pressure. The residue was partitioned between ethyl acetate (100 ml) and 2N hydrochloric acid (50 ml). The mixture was extracted into ethyl acetate and the combined extracts were dried over anhydrous magnesium sulfate, filtered and concentrated under reduced pressure. The product was used directly in the next step without further purification (6.32 g).

MS (EI) 230, 232 (M)$^+$ $^1$H NMR (CDCl$_3$) 7.39(2H, d); 6.83(2H, d); 4.50–4.41 (1H, m); 3.77–3.70(2H, m) 1.93(1H, br); 1.26(3H, d).

c) (2S,3RS)-2-(4-Bromophenoxy)-5-pyridin-3-yl-pent-4-yn-3-ol

Oxalyl chloride (4.38 ml) was added dropwise to a solution of dimethylsulfoxide (4.4 ml) in dry dichloromethane (250 ml) at −60° C. The resulting solution was stirred for 20 minutes and then a solution of (2S)-2-(4-bromophenoxy)-1-propanol (9.24 g, Example 15b) in dry dichloromethane (75 ml) was added dropwise. The mixture was stirred for a further 30 minutes and then triethylamine (22.4 ml) was added dropwise. The mixture was allowed to reach room temperature with stirring over 1 hour. The mixture was diluted with anhydrous ether (100 ml), filtered and concentrated under reduced pressure. The residue was dissolved in dry tetrahydrofuran (20 ml) and added to a solution of 1-lithio-2-(pyridin-3-yl)acetylene [generated by the addition of n-butyllithium (2.5 M in hexanes, 24 ml) to a solution of (pyridin-3-yl)acetylene (6.3 g) (J. Amer. Chem. Soc. 1935, 57, 1284) in tetrahydrofuran (40 ml) at −60° C. with stirring for 20 minutes]. The mixture was stirred for 1 hour at −60° C. and was then allowed to warm to room temperature over 2 hours. The mixture was poured into saturated ammonium chloride solution (100 ml) and extracted with ethyl acetate (3×100 ml). The combined organic extracts were dried over anhydrous magnesium sulfate, filtered and concentrated under reduced pressure. The residue was purified by column chromatography over silica eluting with ethyl acetate:hexane (1:4) and then ethyl acetate to give the sub-title compound as an oil and as a 4:1 mixture of diastereomers (8.31 g).

MS (APCI) 332, 334 (M+H)$^+$ $^1$H NMR (CDCl$_3$, major diastereomer) 8.73(1H, d); 8.53 (1H, dd); 7.74–7.70(1H, m); 7.39(2H, d);7.29–7.24(1H, m); 8.67(2H, d); 4.82–4.78(1H, m); 4.57–4.53(1H, br); 1.45(3H, d).

d) (2S,3RS)-2-(4-Bromophenoxy)-5-pyridin-3-ylpentan-3-ol (2S,3RS)-2-(4-Bromophenoxy)-5-pyridin-3-ylpent-4-yn-3-ol (5.93 g, Example 15c)) was dissolved in ethyl acetate (100 ml) and hydrogenated at 5 atmospheres using 5% rhodium on charcoal (2.0 g) as catalyst. The mixture was filtered through Celite® and the filtrate concentrated under reduced pressure to give the sub-title compound as an oil and as a 4:1 mixture of diastereomers (5.6 g). The diastereomers were separated using normal-phase HPLC eluting with 3% isopropyl alcohol in dichloromethane to give (2S,3R)-2-(4-bromophenoxy)-5-(pyridin-3-yl)-3-pentanol as the major diastereomer (3.21 g) and (2S,3S)-2-(4-bromophenoxy)-5-(pyridin-3-yl)-3-pentanol as the minor diastereomer (0.71 g).

MS (APCI) 336/338 (M+H)$^+$ $^1$H NMR (CDCl$_3$, major diastereomer) 8.50(1H, d); 8.45 (1H, dd); 7.54(1H, dt); 7.37(2H, d); 7.22(1H, dd); 6.76(2H, d); 4.30–4.27(1H, m); 3.82(1H, p); 2.94–2.89(1H, m); 2.77–2.70(1H, m); 2.18(1H, br); 1.86–1.78(2H, m); 1.26 (3H, d).

e) (3R,4S)-3-[4-(4-Bromo-phenoxy)-3-(tert-butyl-dimethyl-silanyloxy)-pentyl]-pyridine To a solution of (2S,3R)-2-(4-bromophenoxy)-5-pyridin-3-ylpentan-3-ol (2.01 g, Example 15d)) in dry dichloromethane (50 ml) was added tert-butyldimethylsilyl chloride (1.81 g) and imidazole (0.814 g) and the resulting solution stirred for 24 hours, concentrated and the residue purified by column chromatography on silica gel eluting with dichloromethane:diethyl ether (1:1) to afford the sub-title compound as an oil (2.52 g).

MS (APCI) 450.1/452.1 (M+H)$^+$ $^1$H NMR (CDCl$_3$) 8.45–8.42(2H, m); 7.4(1H, dt); 7.35 (2H, d); 7.22–7.18 (1H, m); 6.73(2H, d); 4.23–4.20(1H, m); 3.82–3.78(1H, m); 2.84–2.62(2H, m); 1.96–1.88 (1H, m); 1.82–1.78 (1H, m);1.27(3H, d); 0.94 (9H, s); 0.12 (3H, s); 0.09 (3H, s).

f) (1S,2R)-4-[2-(tert-Butyldimethylsilanyloxy)-1-methyl-4-pyridin-3-yl-butoxy]benzeneboronic acid A solution of tert-butyllithium (3.95 ml, 1.7M in hexanes) was added over a 1 hour period to a solution of (2S,3R)-2-(4-bromophenoxy)-3-tert-butyldimethylsilyloxy-5-pyridin-3-ylpentane (2.518 g, Example 15e)) and tri-isopropylborate (1.68 ml) in tetrahydrofuran (20 ml) at −78° C. The resulting solution was stirred at −78° C. for 2 hours and was then quenched by the addition of a saturated solution of ammonium chloride in water (50 ml). The mixture was poured into water (50 ml) and extracted into ethyl acetate (2×50 ml). The combined extracts were dried over anhydrous magnesium sulfate, filtered and evaporated. The residue was purified by chromatography on silica gel eluting with ethyl acetate and then ethyl acetate:methanol (4:1) to afford the sub-title compound as a foam (1.22 g).

MS (APCI) 416 (M+H)$^+$ $^1$H NMR (CDCl$_3$) 8.60–8.53 (2H, m); 7.95 (2H, d); 7.6–7.54 (1H, m) 7.26–7.22 (1H, m); 6.86 (2H, d); 4.33–4.27 (1H, m); 3.93–3.86 (1H, m); 2.82–2.62 (2H, m); 1H, m); 1.28 (3H, d); 0.94 (9H, s); 0.08 (6H, s).

g) 4-[4-(2,4-Dimethoxy-pyrimidin-5-yl)-phenoxy]-1-pyridin-3-yl-pentan-3-ol.

Toluene (4 ml), 2M aqueous sodium carbonate (0.5 ml), (1S,2R)-4-[2-(tert-butyldimethylsilanyloxy)-1-methyl-4-pyridin-3-ylbutoxy]benzeneboronic acid (0.200 g, example 15f)), and tetrakis(triphenylphosphine)palladium(0) (0.020 g) were added to a solution of 5-bromo-2,4-dimethoxypyrimidine (0.209 g) in ethanol (1 ml). The mixture was heated at 120° C. for 4 hours.

After cooling, the solution was concentrated under reduced pressure. Concentrated hydrochloric acid (1 ml) was added to a solution of the residue in methanol (4 ml) and the suspension was stirred at room temperature for 1.5 hours. The mixture was concentrated under reduced pressure and the residue partitioned between diethyl ether and water. The aqueous layer was basified with aqueous sodium bicarbonate solution and the aqueous solution was extracted with ethyl acetate. The combined organic extracts were dried over anhydrous magnesium sulfate, filtered and concentrated under reduced pressure. The residue was purified by normal-phase HPLC eluting with a gradient of 0–25% ethanol in dichloromethane to give the title compound as an oil (0.168 g).

MS (APCI) 396 (M+H)+

$^1$H NMR (DMSO) 8.44(1H, d); 8.38(1H, d); 8.31(1H, s); 7.62(1H, d); 7.41(2H, d); 7.32–7.27(1H, m); 7.96(2H, d); 5.00(1H, d); 4.35–4.28(1H, m); 3.92(6H, s); 3.59–3.32(1H, m); 2.85–2.75(1H, m); 2.69–2.60(1H, m); 1.91–1.80(1H, m); 1.69–1.57(1H, m); 1.23(3H, d).

EXAMPLE 16
(1S,2R)-5-[4-(2-Hydroxy-1-methyl-4-pyridin-3-yl-butoxy)-phenyl]-1H-pyridin-2-one

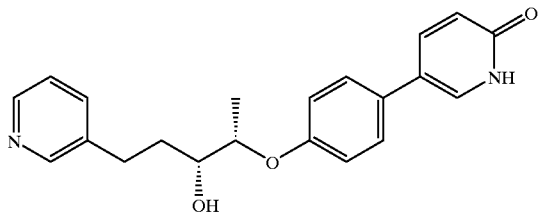

Prepared according to the method described in Example 15g) from toluene (4 ml), 2M aqueous sodium carbonate (0.5 ml), (1S,2R)-4-[2-(tert-butyldimethylsilanyloxy)-1-methyl-4-pyridin-3-yl-butoxy]benzeneboronic acid (0.200 g, Example 15f)), ethanol (1 ml), 5-bromopyridin-2-one (0.221 g) and tetrakis(triphenylphosphine)palladium(0) (0.020 g) with heating at 120° C. for 8 hours.

The product was purified by normal-phase HPLC eluting with a gradient of 0–25% ethanol in dichloromethane to give the title compound as a foam (0.041 g).

m.p. 70–73° C.

MS (APCI) 351 (M+H)+

$^1$H NMR (DMSO) 11.73(1H, bs); 8.43(1H, d); 8.38(1H, d); 7.75(1H, dd); 7.62(1H, d); 7.58(1H, d); 7.42(2H, d); 7.31–7.28(1H, m); 6.93(2H, d); 6.40(1H, d); 4.98(1H, d); 4.30–4.27(1H, m); 3.58–3.48(1H, m); 2.85–2.75(1H, m); 2.69–2.59(1H, m); 1.92–1.78(1H, m); 1.71–1.56(1H, m); 1.21(3H, d).

EXAMPLE 17
(1S,2R)-5-[4-(2-Hydroxy-1-methyl-4-pyridin-3-ylbutoxy)phenyl]-1-methyl-1H-pyridin-2-one

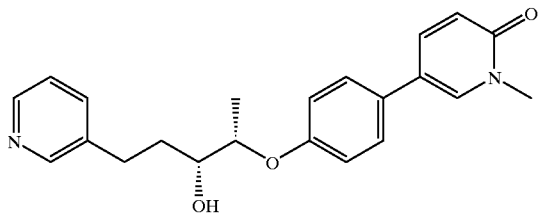

Prepared according to the method described in Example 15g) from toluene (4 ml), 2M aqueous sodium carbonate (0.5 ml), (1S,2R)-4-[2-(tert-butyldimethylsilanyloxy)-1-methyl-4-pyridin-3-yl-butoxy]benzeneboronic acid (0.200 g, example 15f)), ethanol (1 ml), 5-bromo-1-methylpyridin-2-one (0.235 g, Example 13a)) and tetrakis (triphenylphosphine)palladium(0) (0.020 g) with heating at 120° C. for 8 hours.

The product was purified by normal-phase HPLC eluting with a gradient of 0–25% ethanol in dichloromethane to give the title compound as an hygroscopic foam (0.173 g).

MS (APCI) 365 (M+H)+

$^1$H NMR (DMSO) 8.43(1H, s); 8.38(1H, d); 8.01(1H, d); 7.74(1H, d); 7.63(1H, d); 7.44(2H, d); 7.32–7.27(1H, m); 6.95(2H, d); 6.44(1H, d); 4.98(1H, d); 4.33–4.25(1H, m); 3.58–3.48(1H, m); 3.46(3H, s); 2.83–2.73(1H, m); 2.69–2.59(1H, m); 1.91–1.77(1H, m); 1.70–1.55(1H, m); 1.22(3H, d).

EXAMPLE 18
(3R,4S)-4-[4-(6-Dimethylaminopyridin-2-yl)-phenoxy]-1-pyridin-3-ylpentan-3-ol

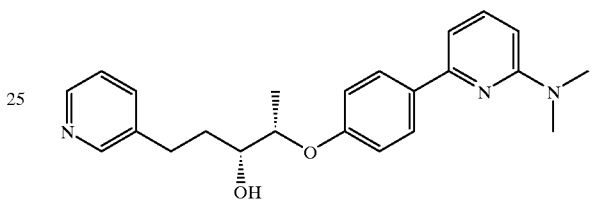

a) 6-Bromo-2-N,N-dimethylaminopyridine 2,6-Dibromopyridine (20 g) was dissolved in ethanol (250 ml). Dimethylamine (40% solution in water, 21.2 ml) was added and the reaction mixture was heated at reflux for 24 hours.

After cooling, the solution was concentrated under reduced pressure. Water (50 ml) was added and the reaction mixture was extracted with ethyl acetate. The combined organics were dried over anhydrous magnesium sulfate, filtered and concentrated under reduced pressure to give the sub-title compound as an oil (16.1 g).

MS (APCI) 201 (M+H)+

$^1$H NMR (DMSO) 7.39(1H, t); 6.70(1H, d); 6.59(1H, d); 2.99(6H, s).

b) (3R,4S)-4-[4-(6-Dimethylaminopyridin-2-yl)phenoxy]-1-pyridin-3-ylpentan-3-ol

Prepared according to the method described in Example 15g) from toluene (4 ml), 2M aqueous sodium carbonate (0.5 ml), (1S,2R)-4-[2-(tert-butyldimethylsilanyloxy)-1-methyl-4-pyridin-3-yl-butoxy]benzeneboronic acid (0.200 g, Example 15f)), ethanol (1 ml), 6-bromo-2-N,N-dimethylaminopyridine (0.201 g, Example 18a)) and tetrakis (triphenylphosphine)palladium(0) (0.020 g) with heating at 120° C. for 4 hours. The product was purified by normal-phase HPLC eluting with a gradient of 0–25% ethanol in dichloromethane to give the title compound as an oil (0.091 g).

MS (APCI) 378 (M+H)+

$^1$H NMR (DMSO) 8.43(1H, s); 8.38(1H, d); 7.95(2H, d); 7.63(1H, d); 7.52(1H, t); 7.32–7.27(1H, m); 7.04(1H, d); 6.95(2H, d); 6.52(1H, d); 4.98(1H, d); 4.37–4.29(1H, m); 3.60–3.51(1H, m); 3.08 (6H, s); 2.84–2.76(1H, m); 2.69–2.61(1H, m); 1.91–1.81(1H, m); 1.69–1.58(1H, m); 1.24(3H, d).

EXAMPLE 19

(2R)-1-[4-(6-Dimethylaminopyridin-2-yl)-phenoxy]-4-pyridin-3-ylbutan-2-ol

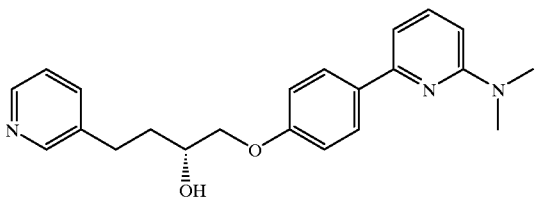

Prepared according to the method described in Example 7c) from 6-bromo-2-N,N-dimethylaminopyridine(Example 18a)), 0.201 g), ethanol (1 ml), toluene (4 ml), 2M aqueous sodium carbonate (0.5 ml), (2R)-4-[2-(tert-butyldimethylsilanyloxy)-4-pyridin-3-yl-butoxy]benzeneboronic acid (Example 7b), 0.200 g), and tetrakis (triphenylphosphine)palladium(0) (0.02 g) with heating at 120° C. for 4 hours. After work-up, the product was purified by normal-phase HPLC eluting with a gradient of 0–25% ethanol in dichloromethane to give the title compound as an oil (0.091 g).

MS (APCI) 364 (M+H)$^+$ $^1$H NMR (DMSO) 8.46(1H, d); 8.40(1H, d); 7.98(2H, d); 7.65(1H, d); 7.53(1H, t); 7.33–7.29(1H, m); 7.07(1H, d); 6.99(2H, d); 6.54(1H, d); 5.07(1H, d); 3.93(2H, d); 3.82–3.76(1H, m); 3.08(6H, s); 2.83–2.63(2H, m); 1.88–1.70(2H, m).

EXAMPLE 20

(2R)-5-[4-(2-Hydroxy-4-pyridin-3-ylbutoxy)phenyl]thiophene-2-sulfonic acid amide.

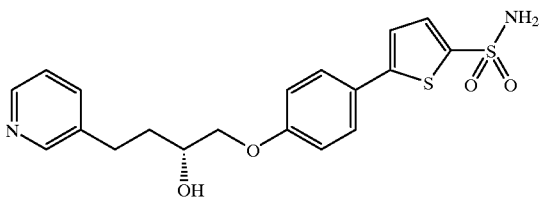

2M Aqueous sodium carbonate (2.5 ml), (2R)-4-[2-(tert-butyldimethylsilanyloxy)-4-pyridin-3-yl-butoxy]benzeneboronic acid (Example 7b)), 1.0 g), and tetrakis (triphenylphosphine)palladium(0) (0.1 g) were added to a solution of 5-bromothiophene-2-sulfonic acid amide (1.21 g) in ethanol (25 ml). The mixture was heated at 90° C. for 4 hours. The mixture was cooled to room temperature and solvents were evaporated under reduced pressure. The reaction mixture was triturated with acetone (10 ml) and filtered through a short silica gel column. The column was eluted with a further 10 ml of acetone. The filtrate was evaporated before purification by normal-phase HPLC, eluting with a gradient of 0–10% ethanol in dichloromethane. The oil obtained was dissolved in methanol (25 ml), 2M hydrochloric acid (10 ml) was added and the solution stirred overnight at room temperature. The solid was filtered off, washed with methanol, water, and then diethyl ether. The product was liberated from its hydrochloride salt by stirring in 2M sodium hydrogencarbonate for 30 minutes. The resulting solid was collected by filtration and washed sequentially with water and diethyl ether to afford the title compound as a solid (0.56 g).

m.p. 197–198° C.

MS (APCI) 405 (M+H)$^+$ $^1$H NMR (DMSO) 8.46(1H, s); 8.40(1H, d); 7.66–7.61 (5H, m); 7.50(1H, d); 7.38(1H, d); 7.32–7.29(1H, m); 7.02 (2H, d); 5.08(1H, bs); 3.93(2H, d); 3.79–3.78(1H, m); 2.82–2.77(1H, m); 2.71–2.66(1H, m); 1.86–1.82(1H, m); 1.74–1.70(1H, m).

EXAMPLE 21

(1S,2R)-5-[4-(2-Hydroxy-1-methyl-4-pyridin-3-yl-butoxy)-phenyl]-thiophene-2-sulfonic acid amide

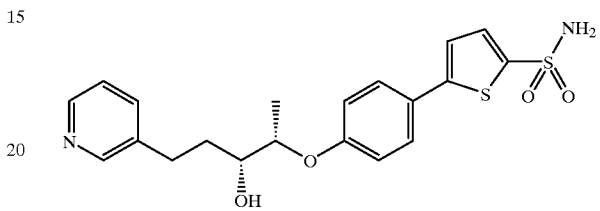

a) (1S,2R)-4-(2-Hydroxy-1-methyl-4-pyridin-3-yl-butoxy)benzeneboronic acid (1S,2R)-4-[2-(tert-butyldimethylsilanyloxy)-1-methyl-4-pyridin-3-yl-butoxy]benzeneboronic acid (10 g, Example 15f)) was stirred for 16 hours at room temperature in a solution of methanol (150 ml) and 2M aqueous hydrochloric acid (25 ml). The solution was concentrated to give an acidic aqueous residue which was washed with diethyl ether. The aqueous layer was basified with saturated sodium bicarbonate, the product was extracted into ethyl acetate, dried over anhydrous magnesium sulfate, filtered and concentrated to give the sub-title compound as a foam. (6.97 g).

MS (APCI) 302 (M+H)$^+$ $^1$H NMR (DMSO/D$_2$O) 8.42(1H, s); 8.39(1H, s); 7.70–7.64(3H, m); 7.33(1H, dd); 6.85(2H, d); 4.32(1H, m); 3.53(1H, m); 2.79(1H, m); 2.66(1H, m); 1.84(1H, m); 1.65 (1H, m); 1.21(3H, d).

b) (1S,2R)-5-[4-(2-Hydroxy-1-methyl-4-pyridin-3-yl-butoxy)-phenyl]-thiophene-2-sulfonic acid amide 2M Aqueous sodium carbonate (0.75 ml), (1S,2R)-4-(2-hydroxy-1-methyl-4-pyridin-3-ylbutoxy)benzeneboronic acid (Example 21a)), 0.19 g), and tetrakis (triphenylphosphine)palladium(0) (0.025 g) were added to a solution of 5-bromothiophene-2-sulfonic acid amide (0.242 g) in ethanol (2 ml). The mixture was heated at 90° C. for 2 hours. The mixture was cooled to room temperature and the solvents were evaporated under reduced pressure. The reaction mixture was triturated with acetone (10 ml) and filtered through a short silica gel column. The column was eluted with acetone and the resulting filtrate evaporated to give the title compound as a solid (0.064 g).

m.p. 184–186° C.

MS (APCI) 419 (M+H)$^+$ $^1$H NMR (DMSO) 8.44 (1H, s); 8.38 (1H, d); 7.67–7.58 (5H, m); 7.49 (1H, d); 7.36 (1H, d); 7.29 (1H, dd); 6.98 (2H, d); 5.01 (1H, d); 4.35 (1H, p); 3.58–52 (1H, m); 2.85–2.73 (1H, m); 2.69–2.59 (1H, m); 1.86–1.80 (1H, m); 1.69–1.61 (1H, m); 1.23 (3H, d).

EXAMPLE 22
(3R,4S)-4-[4-(2-Methoxypyridin-3-yl)phenoxy]-1-pyridin-3-yl-pentan-3-ol.

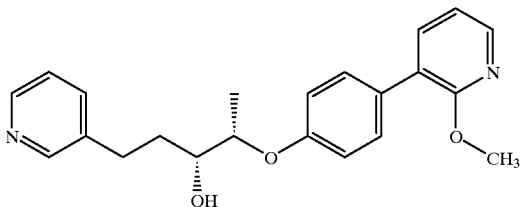

Prepared according to the method described in Example 21b) from 2M aqueous sodium carbonate (2.0 ml), (1S,2R)-4-(2-hydroxy-1-methyl-4-pyridin-3-ylbutoxy)benzeneboronic acid (Example 21a), 0.508 g), 3-iodo-2-methoxypyridine (0.730 g, *J. Org. Chem.*, 1988 53(12), 2740), and tetrakis(triphenylphosphine)palladium(0) (0.216 g) in ethanol (10 ml). The mixture was heated at reflux for 6 hours. After cooling to room temperature the mixture was concentrated under reduced pressure. The residue was purified by column chromatography over silica eluting with ethyl acetate to give an oil, which was further purified by normal phase HPLC eluting with 2-propanol:dichloromethane (3:97) to give the title compound as an oil.

MS (APCI) 365 (M+H)$^+$ $^1$NMR (DMSO) 8.45(1H, d); 8.39(1H, dd); 8.13(1H, dd); 7.69(1H, dd); 7.63(1H, d); 7.45(2H, d); 7.30(1H, dd); 7.06 (1H, dd); 6.96(2H, d); 5.01(1H, d); 4.32(1H, quintet); 3.87 (3H, s); 3.6–3.5(1H, m); 2.85–2.75(1H, m); 2.7–2.6(1H, m); 1.95–1.8(1H, m); 1.7–1.6(1H, m); 1.24(3H, d).

EXAMPLE 23
(3R,4S)-4-[4-(2-Dimethylaminopyridin-3-yl)phenoxy]-1-pyridin-3-ylpentan-3-ol

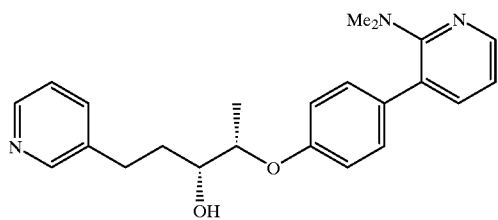

a) 3-Iodo-2-dimethylaminopyridine

This was prepared according to the experimental procedure outlined in *J. Org. Chem.* 1988, 53(12), 2740 by Estel, L. et. al. from 2-fluoro-3-iodopyridine (4.5 g) and 40% aqueous dimethylamine (170 ml). This gave after Kugelrohr distillation (oil pump) the sub-titled compound (4.18 g) as an oil.

GC-MS (ESI) 248(M)$^+$ $^1$H NMR (DMSO) 8.22 (1H,dd); 8.15 (1H, dd); 6.71 (1H, dd); 2.84 (6H, s).

b) (3R,4S)-4-[4-(2-Dimethylaminopyridin-3-yl)phenoxy]-1-pyridin-3-ylpentan-3-ol

Prepared according to the method described in Example 21b) from 3-iodo-2-dimethylaminopyridine (Example 23a), 0.253 g), ethanol (3 ml), 2M aqueous sodium carbonate (0.5 ml), (1S,2R)-4-(2-hydroxy-1-methyl-4-pyridin-3-ylbutoxy)benzeneboronic acid (Example 21a), 0.200 g), and tetrakis(triphenylphosphine)palladium(0) (0.02 g) with heating at 90° C. for 3 hours.

After work-up, the product was purified by normal-phase HPLC eluting with a gradient of 0–25% ethanol in dichloromethane followed by reverse-phase HPLC eluting with a gradient of 40% to 90% acetonitrile/0.1% ammonium acetate to give the title compound as an oil (0.089 g).

MS (APCI) 378 (M+H)$^+$ $^1$H NMR (DMSO) 8.44 (d, 1H); 8.37 (dd, 1H); 8.09 (dd, 1H); 7.63 (dt, 1H), 7.43 (dd, 1H); 7.36 (bd, 2H); 7.30 (dd, 1H), 6.98 (bd, 2H); 6.87 (dd, 1H); 5.00 (d, 1H); 4.31 (p, 1H); 3.55(m, 1H); 2.70–2.90 (m, 1H); 2.60–2.70 (m, 1H); 2.61 (s, 6H); 1.80–1.90 (m, 1H), 1.60–1.70 (m, 1H); 1.23 & 1.25 (d, 3H).

EXAMPLE 24
(3R,4S)-4-[4-(2-Methoxypyridin-4-yl)phenoxy]-1-pyridin-3-yl-pentan-3-ol.

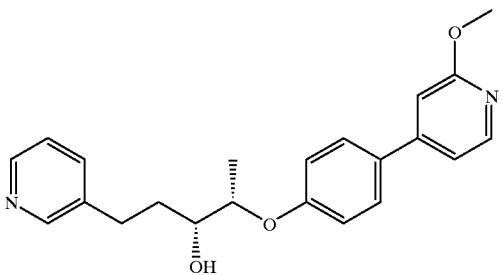

Prepared according to the method described in Example 21b) from (1S,2R)-4-(2-hydroxy-1-methyl-4-pyridin-3-ylbutoxy)benzeneboronic acid (0.150 g, Example 21a), 4-iodo-2-methoxypyridine (0.235 g, *Liebigs Annalen der Chemie* (1992) Issue 9, 953–9), ethanol (3 ml), 2M aqueous sodium carbonate (0.5 ml) and tetrakis(triphenylphosphine)palladium(0) (0.025 g) with heating at 90° C. for 4 hours. After work up, the residue was purified by normal-phase HPLC, eluting with a gradient of 0–25% ethanol in dichloromethane to give the title compound as an oil (0.069 g).

MS (APCI) 365 (M+H)$^+$

NMR (CDCl$_3$) 8.51 (1H, m); 8.45 (1H, m); 8.19 (1H, d); 7.56 (3H, d); 7.25–7.20 (1H, m); 7.07 (1H, m); 6.95 (2H, d); 6.91 (1H, s); 4.45–4.35 (1H, m); 3.96 (3H, s); 3.90–3.83 (1H, m); 3.00–2.90 (1H, m); 2.80–2.70 (1H, m); 2.10(1H, d); 1.90–1.80 (2H, m); 1.31 (3H, d).

EXAMPLE 25
(1S,2R)-5-[4-(2-Hydroxy-1-methyl-4-pyridin-3-yl-butoxy)phenyl]nicotinonitrile.

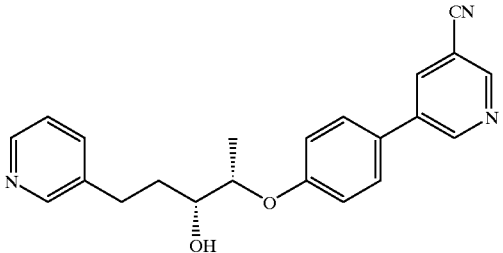

Prepared according to the method described in Example 21b) from (1S,2R)-4-(2-hydroxy-1-methyl-4-pyridin-3-ylbutoxy)benzeneboronic acid (0.15 g, Example 21a)), 5-bromopyridine-3-carbonitrile (0.18 g), aqueous sodium carbonate (2M, 0.57 ml) and tetrakis(triphenylphosphine)palladium(0) (0.014 g) in ethanol (5 ml) with heating at 90°

C. for 4 hours. After work up, the residue was purified by normal-phase HPLC eluting with a gradient of 0–10% ethanol in dichloromethane to give the title compound as an oil (0.073 g).

MS(APCI) 360(M+H)+

$^1$H NMR(CDCl$_3$) 8.99(1H, d); 8.81(1H, d); 8.51(1H, d); 8.45(1H, dd); 8.08–8.06 (1H, m); 7.58–7.54(1H, m); 7.48 (2H, d); 7.23–7.21(1H, m); 7.01(2H, d); 4.43–4.40(1H, m); 3.86(1H, m); 2.96–2.91(1H, m); 2.80–2.72(1H, m); 2.15 (1H, m); 1.90–1.83 (2H, m); 1.32(3H, d).

EXAMPLE 26
(2R)-5-[4-(2-Hydroxy-4-pyridin-3-yl-butoxy)phenyl] nicotinonitrile.

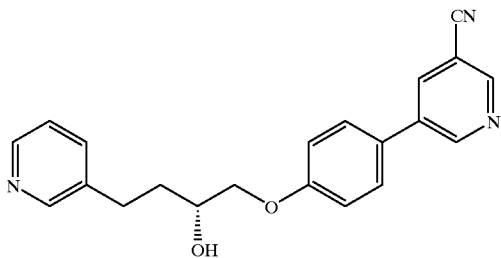

Prepared according to the method described in Example 21b) from (2R)-4-(2-hydroxy-4-pyridin-3-ylbutoxy) benzeneboronic acid (0.15 g, Example 28a)), 5-bromopyridine-3-carbonitrile (0.19 g), 2M aqueous sodium carbonate (0.60 ml) and tetrakis (triphenylphosphine)palladium(0) (0.014 g) with heating at 90° C. for 4 hours. After work up, the residue was purified by normal-phase HPLC eluting with a gradient of 0–10% ethanol in dichloromethane to give the title compound as an oil (0.10 g).

MS(APCI) 346(M+H)+

$^1$H NMR (CDCl$_3$) 8.99(1H, d); 8.81(1H, d); 8.53(1H, d); 8.47(1H, dd); 8.08(1H, t); 7.59–7.54(1H, m); 7.52(2H, d); 7.26–7.22(1H, m); 7.03(2H, d); 4.04–4.0(2H, m); 3.96–3.90 (1H, m); 2.98–2.78(2H, m); 2.39(1H, d); 1.97–1.90(2H, m).

EXAMPLE 27
(3R,4S)-4-[4-(6-Methoxy-pyridin-2-yl)-phenoxy]-1-pyridin-3-yl-pentan-3-ol

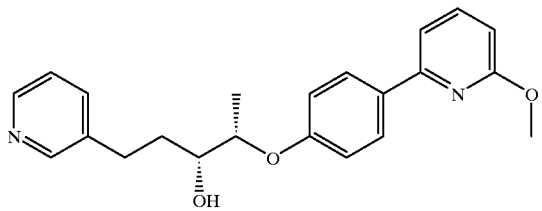

Prepared according to the method described in Example 21b) from 2M aqueous sodium carbonate (0.66 ml), (1S, 2R)-4-(2-hydroxy-1-methyl-4-pyridin-3-ylbutoxy) benzeneboronic acid (Example 21a), 0.200 g), 6-bromo-2-methoxypyridine (J. Org. Chem., 55, 1, 1990, 69–73; 0.250 g) and tetrakis(triphenylphosphine)palladium(0) (0.020 g) in ethanol (3 ml). The mixture was heated at 90° C. for 2 hours.

After work-up, the product was purified by normal-phase HPLC eluting with a gradient of 0–10% ethanol in dichloromethane to give an oil, which was further purified by column chromatography over silica eluting with dichloromethane:acetone (2:1) to give the title compound as an oil (0.145 g).

MS(APCI) 365(M+H)+

$^1$H NMR(DMSO) 8.44(1H,d); 8.38(1H, dd); 8.01(2H, d); 7.72(1H, t); 7.63(1H, dt); 7.45(1H, d); 7.32–7.28(1H, m); 6.99(2H, d); 6.69(1H, d); 5.01(1H, d); 4.40–4.32 (1H, m); 3.93(3H, s); 3.59–3.54(1H, m); 2.85–2.73(1H, m); 2.72–2.60(1H, m); 1.91–1.80(1H, m); 1.71–1.59(1H, m); 1.24(3H, d).

EXAMPLE 28
(2R)-1-[4-(6-Methoxy-pyridin-2-yl)-phenoxy]-4-pyridin-3-yl-butan-2-ol

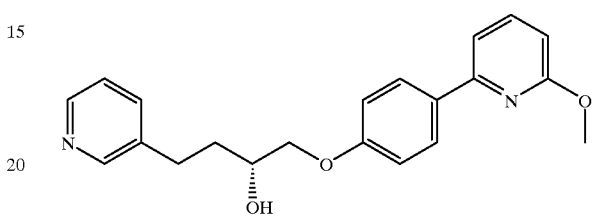

a) (2R)-4-[2-Hydroxy-4-pyridin-3-ylbutan-2-oxy] benzeneboronic acid

2M Hydrochloric acid solution (5.6 ml) was added to a solution of (1S,2R)-4-[2-(tert-butyldimethylsilanyloxy)-1-methyl-4-pyridin-3-yl-butoxy]benzeneboronic acid (Example 7b)), 1.5 g) in methanol (40 ml). The reaction mixture was stirred overnight at room temperature, then concentrated under reduced pressure. 2M Hydrochloric acid solution (3 ml) was added and the aqueous layer was washed with diethyl ether (3×5 ml). The aqueous layer was basified with 2M sodium hydroxide solution and extracted with ethyl acetate (3×15 ml). The combined organic extracts were dried over anhydrous magnesium sulfate, filtered and concentrated under reduced pressure to give the sub-title product as a white foam (0.68 g).

MS (APCI) 288 (M+H)+

$^1$H NMR (DMSO) 8.45(1H, s); 8.40(1H, d); 7.83(1H, s); 7.72–7.64(2H, m); 7.32–7.18(1H, m); 6.93–6.72(2H, m); 5.04(1H, d); 4.07–4.00(1H, m); 3.92–3.75(2H, m); 2.92–2.63 (2H, m); 1.83–1.66 (2H, m).

b) (2R)-1-[4-(6-Methoxypyridin-2-yl)phenoxy]-4-pyridin-3-yl-butan-2-ol.

2M Aqueous sodium carbonate (0.66 ml), (2R)-4-(2-hydroxy-4-pyridin-3-ylbutoxy)benzeneboronic acid (Example 28b)), 0.19 g), and tetrakis(triphenylphosphine) palladium(0) (0.02 g) were added to a solution of 6-bromo-2-methoxypyridine (J. Org. Chem., 55, 1, 1990, 69–73; 0.248 g) in ethanol (3 ml). The mixture was heated at 90° C. for 5 hours. After work-up, the residue was purified by normal-phase HPLC, eluting with a gradient of 0–10% ethanol in dichloromethane to give the title compound as a solid (0.127 g).

m.p. 87° C.

MS (APCI) 351(M+H)+

$^1$H NMR (DMSO) 8.47(1H, s); 8.40(1H, d); 8.03(2H, d); 7.73(1H, t); 7.66 (1H, d); 7.47(1H, d); 7.32(1H, t); 7.03(2H, d); 6.69(1H, d); 5.09(1H, d); 3.94(5H, m); 3.80(1H, br.s); 2.90–2.74(1H, m); 2.72–2.65(1H, m); 1.93–1.82(1H, m); 1.79–1.68(1H, m).

EXAMPLE 29

(1S,2R)-4-[4-(2-Hydroxy-1-methyl-4-pyridin-3-yl-butoxy)phenyl]-(1H)-pyridin-2-one

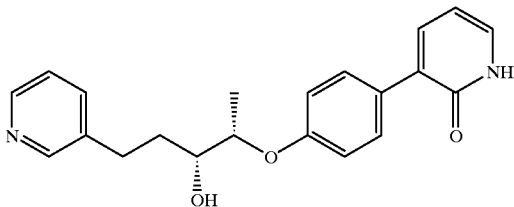

a) 3-Iodo-2-pyridone

A solution of 3-iodo-2-fluoropyridine (2.5 g, *J. Org. Chem.*, 1988 53(12), 2740) in ethanol (60 ml) was treated with concentrated hydrochloric acid (30 ml) and then heated at reflux for 5 hours. The solution was then concentrated under reduced pressure to remove the ethanol. The residue was neutralised with 2M aqueous sodium hydroxide and the aqueous solution saturated with sodium chloride. The solution was extracted with ethyl acetate, the combined extracts dried over anhydrous magnesium sulfate, filtered and concentrated under reduced pressure. The residue was purified by chromatography over silica eluting with dichloromethane then ethyl acetate to give a solid that was crystallised from 2-propanol/hexane to give a yellow solid (1.08 g).

MS (APCI) 222 (M+H)$^+$ $^1$H NMR (DMSO) 11.94(1H, br s); 8.10(1H, dd); 7.45 (1H, dd); 5.99(1H, t).

b) (1S,2R)-4-[4-(2-Hydroxy-1-methyl-4-pyridin-3-yl-butoxy)phenyl]-(1H)-pyridin-2-one.

Prepared according to the method described in Example 21b) from 2M aqueous sodium carbonate (0.5 ml), (2R)-4-(2-hydroxy-4-pyridin-3-ylbutoxy)benzeneboronic acid (Example 21a), 0.204 g), 3-iodo-2-pyridone (0.293 g, Example 29a)) tetrakis(triphenylphosphine)palladium(0) (0.050 g) in ethanol (3 ml). The mixture was heated at 90° C. for 4 hours. After cooling to room temperature the mixture was concentrated under reduced pressure. The residue was purified by column chromatography over silica eluting with ethyl acetate:ethanol (4:1) to give an oil, which was further purified by normal phase HPLC eluting with 0 to 25% ethanol in dichloromethane to give an oil. This was then further purified by reverse-phase HPLC eluting a gradient of 25–100% acetonitrile in 0.1 w/v aqueous ammonium acetate solution. This gave an oil which was triturated with ether to give a solid (0.054 g).

m.p. 154–157° C.

MS (APCI) 351 (M+H)$^+$ $^1$H NMR (DMSO) 11.71(1H, br s); 8.5–8.3(2H, m); 7.7–7.6(3H, m); 7.56(1H, dd); 7.35–7.25(2H, m); 6.91(2H, d); 6.26(1H, t); 4.99(1H, d); 4.35–4.25(1H, m); 3.6–3.5(1H, m); 2.9–2.7(1H, m); 2.7–2.6(1H, m); 1.95–1.8(1H, m); 1.7–1.55(1H, m); 1.23(3H, d).

EXAMPLE 30

(3R,4S)-4-(4-[1,3,4]Oxadiazol-2-ylphenoxy)-1-pyridin-3-yl-pentan-3-ol

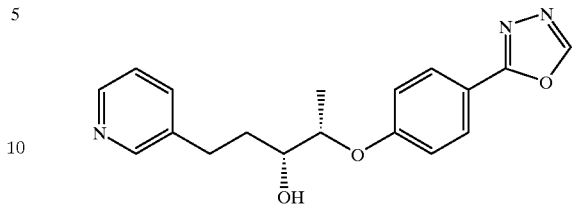

a) (3RS,4R)-4-Benzyloxy-1-pyridin-3-yl-pent-1-yn-3-ol

Butyllithium (2.5M in hexanes, 8.88 ml) was added dropwise at 0° C. to a mechanically stirred solution of 3-pyridylacetylene (prepared by the method of *Synthesis*, 1996, 589–590) in 50 ml diethyl ether. A solution of anhydrous zinc bromide (5 g) in 30 ml diethyl ether (exothermic dissolution) was added dropwise to the reaction mixture at 0° C. (2R)-2-Benzyloxy-propionaldehyde (prepared by the method of *Aust. J. Chem.*, 1995, 48, 1775 and references therein, 3.65 g) in 25 ml anhydrous diethyl ether was added to the reaction mixture at −78° C. and stirred 0.5 hours before allowing to warm to room temperature. After 3 hours water was added and the reaction products were extracted with ethyl acetate. The combined organic phases were washed with water, and brine, dried over anhydrous magnesium sulfate, filtered and concentrated in vacuo. The residue was purified by flash chromatography on silica gel, eluting with isohexane:ethyl acetate 1:1 to give the subtitle compound as an oil (1.745 g).

MS (APCI) 268.1 (M+H)$^+$ $^1$H NMR (CDCl$_3$) (major diastereomer) 8.68 (1H, m); 8.53(1H, m); 7.20 (1H, m); 7.37–7.22 (6H, m); 4.76–4.59 (2H, dd); 4.49 (1H, m); 3.79–3.73 (1H, m); 3.10 (1H, br.d); 1.36 (3H, d).

HPLC (Chiralpak AD, isohexane/isopropanol 9:1) shows 5.3:1 ratio of diastereomers b) (3RS,4R)-3-[4-Benzyloxy-3-(tert-butyldimethylsilanyloxy)-pent-1-ynyl]pyridine (3RS,4R)-4-Benzyloxy-1-pyridin-3-yl-pent-1-yn-3-ol (Example 30b), 1.745 g) was stirred in dimethylformamide (20 ml) with tert-butyldimethylsilyl chloride (1.18 g) and imidazole (0.89 g) at room temperature for 22 hours. Water was added and the reaction was extracted with diethyl ether. The organic phases were combined, washed with brine, dried over anhydrous magnesium sulfate, filtered and concentrated in vacuo. Purification by flash chromatography on silica gel, eluting with 4:1 isohexane/ethyl acetate gave the subtitle compound as an oil (2.014 g).

MS (APCI) 382.2 (M+H)$^+$ $^1$H NMR (CDCl$_3$) (major diastereomer) 8.66 (1H, br.s); 8.52 (1H, br.d); 7.70 (1H, m); 7.39–7.22 (6H, m); 4.69 (2H, s); 4.63 (1H, d); 3.64 (1H, m); 1.28 (3H, d); 0.94 (9H, m); 0.18–0.14 (6H, d).

c) (3RS,4R)-3-[4-Hydroxy-3-(tert-butyldimethylsilanyloxy)pentyl]pyridine.

(3RS,4R)-3-[4-Benzyloxy-3-(tert-butyl-dimethyl-silanyloxy)-pent-1-ynyl]-pyridine (Example 30b), 1.87 g) was refluxed for 50 hours in 1:1 cyclohexene/ethanol (60 ml) with palladium hydroxide (0.75 g). A further 0.50 g catalyst was added and the reaction was refluxed 24 hours, filtered through Celite® and concentrated in vacuo. The product was dissolved in 1,4-cyclohexadiene (6 ml), ethanol (10 ml) and refluxed 48 hours with palladium hydroxide (1.6 g). The reaction mixture was filtered through Celite® and concetrated in vacuo. Purification by flash chromatography on silica gel, eluting with 1:2 isohexane/ethyl acetate gave the subtitle compound as an oil (0.71 g).

MS (APCI) 296.2/297.2/298.2 (M+H)$^+$ $^1$H NMR (CDCl$_3$) 8.44 (2H, br.s); 7.50 (1H, m); 7.21 (1H, m); 3.77 (1H, m); 3.56 (1H, q); 2.67 (2H, m); 2.19 (1H, br.d); 2.00–1.65 (2H, m); 1.15 (3H, d); 0.93 (9H, m) 0.01 (6H, m).

HPLC (Chiralpak AD, isohexane/isopropanol 9:1) 5.4:1 ratio of diastereomers.

d) (3RS,4S)-3-(tert-Butyldimethylsilanyloxy)-4-(4-[1,3,4] oxadiazol-2-yl-phenoxy)pentyl]-pyridine Diethylazodicarboxylate (0.355 ml) was added to a stirred solution of (3RS,4R)-3-[4-hydroxy-3-(tert-butyldimethylsilanyloxy)pentyl]pyridine (Example 30c), 0.606 g), 4-(1,3,4)-oxadiazol-2-yl-phenol (0.333 g), and triphenylphosphine (0.538 g) in toluene at 0° C. The reaction was allowed to warm to room temperature and stirred 16 hours. The reaction mixture was concentrated in vacuo and purified by reverse phase HPLC, eluting with a gradient of 25% to 95% acetonitrile in 0.1 M ammonium acetate to give the subtitle compound as an orange oil (0.300 g).

MS (APCI) 440.2 (M+H)$^+$ e) (3RS,4S)-4-(4-[1,3,4]-Oxadiazol-2-yl-phenoxy)-1-pyridin-3-yl-pentan-3-ol.

A solution of (3RS,4S)-3-(tert-butyldimethylsilanyloxy)-4-(4-[1,3,4]oxadiazol-2-yl-phenoxy)pentyl]pyridine (Example 30d), 0.300 g) and tetrabutylammonium fluoride (1.0M in tetrahydrofuran, 0.751 ml) were stirred 16 hours at room temperature. The reaction was concentrated in vacuo and the residue purified by reverse-phase HPLC, eluting with a gradient of 15% to 95% acetonitrile in 0.1M ammonium acetate. Subsequent purification by normal-phase HPLC, eluting with 0–10% ethanol in dichloromethane gave the title compound as an oil (0.070 g).

MS (APCI) 326.1 (M+H)$^+$

NMR (CDCl$_3$) 8.51 (1H, m); 8.46 (1H, d); 8.42 (1H, s); 8.01 (2H, m); 7.53 (1H, d); 7.25 (1H, m); 6.99 (2H, m); 4.45 (1H, m); 3.87 (1H, m); 2.96 (1H, m); 2.78 (1H, m); 1.84 (2H, m); 1.33 (3H, d).

HPLC (Chiralpak AD, isohexane/isopropanol 9:1) 4.4:1 ratio of diastereomers.

EXAMPLE 31

(2R)-4-[4-(2-Hydroxy-4-pyridin-3-yl-butoxy)-phenyl]-(1H)-pyridin-2-one

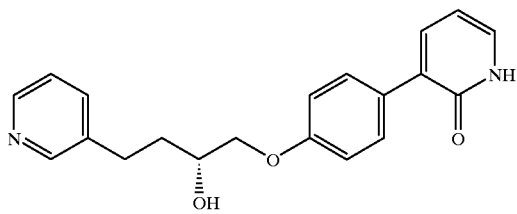

Prepared according to the method described in Example 28b) from 2M aqueous sodium carbonate (1.0 ml), (2R)-4-(2-hydroxy-4-pyridin-3-ylbutoxy)benzeneboronic acid (Example 28a) 0.170 g), 3-iodo-2-pyridone (0.221 g) tetrakis(triphenylphosphine)palladium(0) (0.034 g) in ethanol (3 ml). The mixture was heated at 100° C. for 14 hours. After cooling to room temperature the mixture was concentrated under reduced pressure. The residue was purified by column chromatography over silica eluting with dichloromethane then dichloromethane:ethanol (4:1) to give a solid, which was further purified by reverse-phase HPLC eluting a gradient of 25–100% acetonitrile in 0.1 w/v aqueous ammonium acetate solution. This gave a product that was dissolved in a minimum amount of methanol and then triturated with ether to give a solid (0.070 g).

m.p. 151–154° C.

MS (APCI) 337 (M+H)$^+$ $^1$H NMR (DMSO) 11.72(1H, br s); 8.46(1H, d); 8.39(1H, dd); 7.7–7.65(3H, m); 7.58(1H, dd); 7.35–7.3(2H, m); 6.93 (2H, d); 6.26(1H, t); 5.06(1H, d); 3.90(2H, d); 3.85–3.75 (1H, m); 2.85–2.75(1H, m); 2.75–2.65(1H, m); 1.95–1.8 (1H, m); 1.8–1.65(1H, m).

EXAMPLE 32

(1R,2S)-4-[4-(2-Hydroxy-1-methyl-4-pyridin-3-yl-butoxy)-phenyl]pyrazole-1-sulfonic acid dimethylamide.

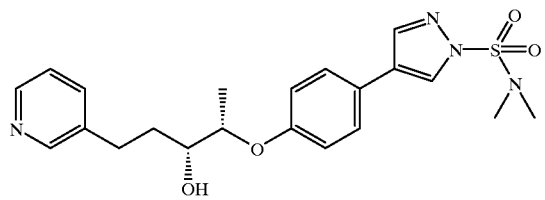

a) 4Bromo-pyrazole-1-sulfonic acid dimethyl amide

Sodium hydride(1.1 g, 60% in mineral oil) was added portionwise to a stirred solution of 4-bromopyrazole (3.7 g) in dry tetrahydrofuran (25 ml) under a nitrogen atmosphere. The mixture was stirred at room temperature for 30 minutes. To this was then added dimethylsulfamoyl chloride, and then heated and stirred at reflux for 2 hours. The reaction was quenched by the addition of water (20 ml), and the organic phase separated. The aqueous phase was extracted into ethyl acetate, the combined organic phases were washed with brine, dried over anhydrous magnesium sulfate, filtered, and the filtrate was concentrated under reduced pressure to give an oil, which was purified by column chromatography over silica, eluting with ethyl acetate:isohexane (1:9) to give the sub-title compound as an oil (6 g).

MS (EI) 255(M+H)$^+$ $^1$H NMR 8.58(1H, s); 8.04(1H, s); 2.87(6H, s).

b) (1R,2S)-4-[4-(2-Hydroxy-1-methyl-4-pyridin-3-yl-butoxy)-phenyl]pyrazole-1-sulfonic acid dimethylamide.

Prepared according to the method described in Example 21b) from (1S,2R)-4-(2-hydroxy-1-methyl-4-pyridin-3-ylbutoxy)benzeneboronic acid (0.2 g, Example 21a)), 4-bromopyrazole-1-sulfonic acid dimethyl amide (0.17 g, Example 32a), ethanol (3 ml), aqueous sodium carbonate (2M, 0.7 ml) and tetrakis(triphenylphosphine)palladium(0) (0.03 g) with heating at 80° C. for 4 hours. After work up, the residue was purified by normal-phase HPLC eluting with a gradient of 0–25% ethanol in dichloromethane to give the title compound as a white foam (0.12 g).

MS (APCI) 431 (M+H)$^+$

NMR (CDCl$_3$) 8.50(1H, d); 8.46(1H, dd); 8.11 (1H, d); 7.94(1H, d); 7.56(1H, dt); 7.42 (2H, dt); 7.24–7.21(1H, m); 6.92(2H, dt); 4.39–4.34(1H, m); 3.87–3.83(1H, m); 2.98–2.91 (7H, m); 2.77–2.72(1H, m); 2.26(1H br.s); 1.92–1.78(2H, m); 1.30(3H, d).

EXAMPLE 33
(2R)-1-[4-(2-Methoxypyridin-3-yl)phenoxy]-4-pyridin-3-ylbutan-2-ol

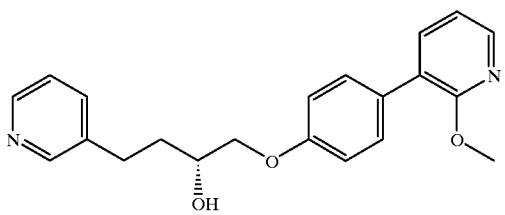

Prepared according to the method described in Example 28b) from 2M aqueous sodium carbonate (1.0 ml), (2R)-4-(2-hydroxy-4-pyridin-3-ylbutoxy)benzeneboronic acid (Example 28a), 0.166 g), 3-iodo-2-methoxypyridine (0.271 g, *J. Org. Chem.*, 1988 53(12), 2740) tetrakis(triphenylphosphine)palladium(0) (0.034 g) in ethanol (3 ml). The mixture was heated at 100° C. for 14 hours. After cooling to room temperature the mixture was concentrated under reduced pressure. The residue was purified by column chromatography over silica eluting with ethyl acetate to give an oil, which was further purified by normal-phase HPLC eluting with 0 to 25% ethanol in dichloromethane to give an oil. This was further purified by reverse-phase HPLC eluting a gradient of 25–100% acetonitrile in 0.1 w/v aqueous ammonium acetate solution to give the title compound as an oil.

MS (APCI) 351 (M+H)$^+$ $^1$H NMR (DMSO) 8.46(1H, d); 8.40(1H, dd); 8.12(1H, dd); 7.70(1H, dd); 7.65(1H, dt); 7.48(2H, d); 7.31(1H, dd); 7.06(1H, dd); 6.99(2H, d); 5.07(1H, d); 3.92(2H, d); 3.87 (3H, s); 3.85–3.75(1H, m); 2.9–2.6(2H, m); 1.95–1.65(2H, m).

EXAMPLE 34
(2R)-4-Pyridin-3-yl-1-(4-pyrimidin-5-yl-phenoxy)butan-2-ol

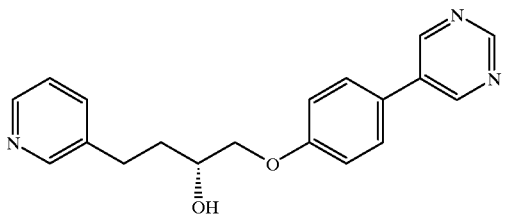

Prepared according to the method described in Example 28b) from 5-bromopyrimidine (0.228 g), ethanol (3 ml), 2M aqueous sodium carbonate (0.5 ml), (2R)-4-(2-hydroxy-4-pyridin-3-ylbutoxy)benzeneboronic acid (Example 28a)), 0.200 g), and tetrakis(triphenylphosphine)palladium(0) (0.05 g) with heating at 100° C. for 5 hours.

After work-up, the product was purified by normal-phase HPLC eluting with a gradient of 0–10% ethanol in dichloromethane to give the title compound as a pale yellow oil (0.080 g).

MS (APCI) 322 (M+H)$^+$ $^1$H NMR (DMSO) 9.12(1H, s); 9.10(2H, s); 8.46(1H, s); 8.40(1H, d); 7.75(2H, d); 7.65(1H, d); 7.33–7.29(1H, m); 7.09(2H, d); 5.09(1H, d); 3.96(2H, d); 3.83–3.77(1H, m); 2.86–2.63(2H, m); 1.87–1.67(2H, m).

EXAMPLE 35
(3R,4S)-1-Pyridin-3-yl-4-(4-pyrimidin-5-yl-phenoxy)pentan-3-ol.

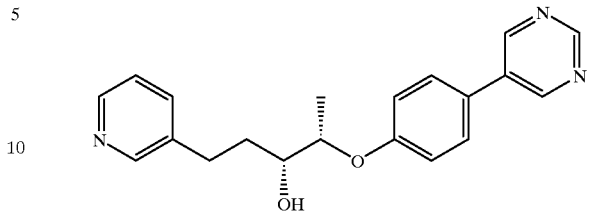

Prepared according to the method described in Example 21b) from (1S,2R)-4-(2-hydroxy-1-methyl-4-pyridin-3-ylbutoxy)benzeneboronic acid (0.200 g, Example 21a)), 5-bromopyrimidine (0.159 g), ethanol (3 ml), 2M aqueous sodium carbonate (0.67 ml) and tetrakistriphenylphosphine palladium(0) (0.030 g) with heating at 90° C. for 4 hours. After work up, the residue was purified by reverse phase HPLC, eluting with a gradient of 15:85 to 95:5 acetonitrile in 0.1M ammonium acetate. The compound was subsequently purified by flash chromatography on silica gel, eluting with 1:1 isohexane/acetone to give the title compound as an oil (0.070 g).

MS (APCI) 336.2 (M+H)$^+$ $^1$H NMR (CDCl$_3$) 9.16 (1H, s); 8.91 (2H, s); 8.52 (1H, br.s); 8.46 (1H, d); 7.57 (1H, d); 7.50 (2H, d); 7.27 (CHCl$_3$); 7.23 (1H, m); 7.03 (2H, d); 4.42 (1H, m); 3.87 (1H, m); 2.96 (1H, m); 2.75 (1H, m); 2.35 (1H, br.s); 1.86 (2H, m); 1.72 (1H, br.s); 1.33 (3H, d).

EXAMPLE 36
(1S,2R)-5-[4-(2-Hydroxy-1-methyl-4-pyridin-3-yl-butoxy)-phenyl]-1-methyl-3-trifluoromethyl-1H-pyridin-2-one

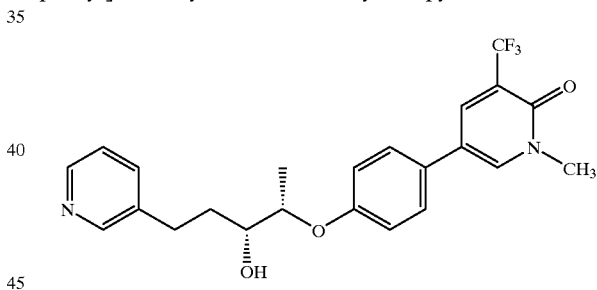

a) 3-(Trifluoromethyl)-5-bromo-2[1H]methylpyridone.

Sodium (0.076 g) was added to dry ethanol (25 ml) at room temperature under nitrogen and stirred until the solution became clear. A solution of 5-bromo-3-(trifluoromethyl)-2-(1H)-pyridone (0.80 g, Patent, JP 79-32068 790319) in ethanol (30 ml) was added dropwise and the resulting solution was stirred at room temperature for 2 hours. Iodomethane (0.25 ml) was added dropwise to the reaction mixture at 5° C. The resulting solution was stirred at room temperature for 22 hours then heated at reflux for 4 hours. The reaction was cooled to room temperature and concentrated under reduced pressure. The residue was dissolved in ethyl acetate (50 ml) and washed with water (2×25 ml). The organic layer was dried over anhydrous magnesium sulfate, filtered and concentrated under reduced pressure to give the sub-title compound as a solid (0.77 g).

m.p. 109–113° C.

MS(GC) 255/257 (M$^+$)

$^1$H NMR(CDCl$_3$) 7.83(1H, d); 7.65(1H, d); 3.60(3H,s).

b) (1S,2R)-5-[4-(2-Hydroxy-1-methyl-4-pyridin-3-yl-butoxy)-phenyl]-1-methyl-3-trifluoromethyl-1H-pyridin-2-one Prepared according to the method described in Example 21b) from (1S,2R)-4-(2-hydroxy-1-methyl-4-pyridin-3-ylbutoxy)benzeneboronic acid (0.20 g, Example 21a)), 3-(trifluoromethyl)-5-bromo-2(1H)-methylpyridone (0.26 g, Example 36a)), 2M aqueous sodium carbonate (0.76 ml) and tetrakis(triphenylphosphine)palladium(0) (0.019 g) in ethanol (5 ml) with heating at 90° C. for 6 hours. After work up, the residue was purified by normal-phase HPLC eluting with a gradient of 0–25% ethanol in dichloromethane to give the title compound as an oil (0.20 g).

MS(APCI) 433 (M+H)$^+$ $^1$H NMR(CDCl$_3$) 8.50(1H, d); 8.46(1H, dd); 7.96(1H, d); 7.63(1H, d); 7.57–7.54 (1H, m); 7.30(2H,d); 7.26–7.21(1H, m); 6.94(2H, d); 4.39–4.36(1H, m); 3.87–3.83(1H, m); 3.66(3H, s); 2.95–2.90(1H, m); 2.79–2.71(1H, m); 2.25(1H, d); 1.89–1.81(2H, m); 1.30(3H, d).

EXAMPLE 37
(2R)-5-[4-(2-Hydroxy-4-pyridin-3-yl-butoxy)-phenyl]-1-methyl-3-trifluoromethyl-1H-pyridin-2-one

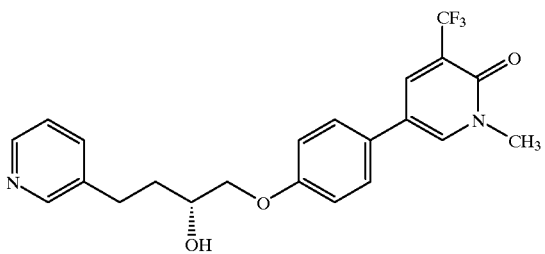

Prepared according to the method described in Example 28b) from (2R)-4-(2-hydroxy-4-pyridin-3-ylbutoxy)benzeneboronic acid (0.20 g, Example 28a)), 3-(trifluoromethyl)-5-bromo-2-(1H)-methylpyridone (0.27 g, Example 36a)), 2M aqueous sodium carbonate (0.76 ml) and tetrakis(triphenylphosphine)palladium(0) (0.039 g) in ethanol (5 ml) with heating at 90° C. for 6 hours. After work up, the residue was purified by normal-phase HPLC eluting with 0–25% ethanol in dichloromethane to give the title compound as a foam (0.10 g).

MS(APCI) 419(M+H)$^+$ $^1$H NMR(CDCl$_3$) 8.52(1H, d); 8.46(1H, dd); 7.96(1H, d); 7.63(1H, d); 7.57(1H, d); 7.31(2H, d); 7.25–7.22(1H, m); 6.96(2H, d); 4.01–3.98(2H, m); 3.92–3.88(1H, m); 3.66(3H, s); 2.96–2.90(1H, m); 2.84–2.78(1H, m); 2.57(1H, br.s); 1.99–1.84(2H, m).

EXAMPLE 38
(3R,4S)-4-[4-(4-Chloro-2-methylamino-pyrimidin-5-yl)-phenoxy]-1-pyridin-3-yl-pentan-3-ol.

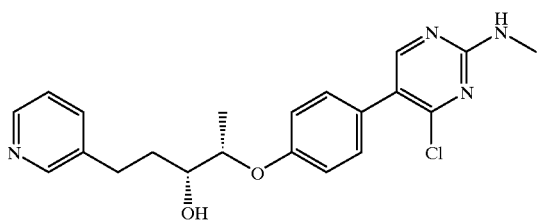

a) (5-Bromo-4-chloropyrimidin-2-yl)methylamine

Methylamine (2M solution in tetrahydrofuran, 3.90 ml) was added to a stirred solution of 5-bromo-2,4-dichloropyrimidine (1.0 ml) in tetrahydrofuran (40 ml) at room temperature for 20 hours. The reaction was worked up by addition of water and extraction into ethyl acetate (3×25 ml). The organic phases were combined, dried over anhydrous magnesium sulfate, filtered and concentrated in vacuo. The residue was purified by flash chromatography on silica gel, eluting with 6:1 isohexane:ethyl acetate to give the subtitle compound as a solid (0.700 g).

m.p. 150.5–151.6° C.

MS (APCI) 222/224/226 (M+H)$^+$ $^1$H NMR (CDCl$_3$) 8.11 (1H, s); 5.61 (1H, br.s); 3.10(3H, d).

b) (3R,4S)-4-[4-(4-Chloro-2-methylamino-pyrimidin-5-yl)-phenoxy]-1-pyridin-3-yl-pentan-3-ol Prepared according to the method described in Example 21b) from (1S,2R)-4-(2-hydroxy-1-methyl-4-pyridin-3-ylbutoxy)benzeneboronic acid (0.200 g, Example 21a)), (5-bromo-4-chloropyrimidin-2-yl)methylamine (Example 38a), 0.159 g), ethanol (3 ml), 2M aqueous sodium carbonate (0.67 ml) and tetrakis(triphenylphosphine)palladium(0) (0.030 g) with heating at 90° C. for 4 hours. After work up, the residue was purified by normal-phase HPLC, eluting with a gradient of 0–10% ethanol in dichloromethane to give the title compound as a foam (0.040 g).

MS (APCI) 399.2 (M+H)$^+$ $^1$H NMR (CDCl$_3$) 8.46 (2H, m); 7.81 (1H, s); 7.56 (1H, d); 7.22 (3H, m); 6.96 (2H, d); 5.24 (1H, br.m); 4.37 (1H, m); 3.84 (1H, m); 3.00 (3H, d); 2.93 (1H, m); 2.74 (1H, m); 2.40 (1H, br.s); 1.87 (2H, m); 1.32 (3H, d).

EXAMPLE 39
(2S)-5(4-(2-Hydroxy-4-pyridin-3-yl-butoxy)phenyl)thiophene-2-sulfonic acid amide.

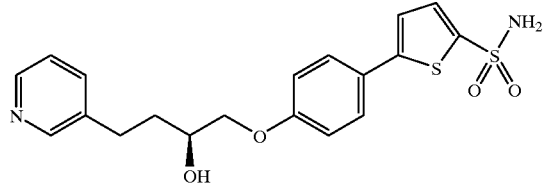

a) (2S,3E/Z)-4-(3-Pyridyl)-1,2-O-isopropylidenebut-3-ene-1,2-diol

A solution of n-butyllithium (2.5 M in hexanes; 12 ml) was added dropwise to a stirred suspension of 3-pyridylmethyltriphenylphosphonium chloride hydrochloride (6.39 g, prepared by the method of *J. Med. Chem.* 1986, 29, 1461) in tetrahydrofuran (50 ml) at –40° C. The resulting mixture was stirred at room temperature for 30 minutes and was then cooled to –70° C. A solution of 2,3-O-(R)-isopropylidene-d-glyceraldehyde (1.82 g) (prepared by the method of *Organic Synthesis* (1995) 72, 6) in tetrahydrofuran (10 ml) was added. The resulting mixture was stirred and allowed to reach room temperature over 3 hours. The mixture was poured into brine (200 ml) and extracted into ethyl acetate. The combined extracts were dried over anhydrous magnesium sulfate, filtered and concentrated under reduced pressure. The residue was purified by column chromatography over silica eluting with diethyl ether to give the sub-title compound as an oil (2.24 g).

MS (EI) 205 (M)$^+$ $^1$H NMR (CDCl$_3$) major Z-diastereomer 8.53(2H, d); 7.61(1H, dt); 7.29(1H, dd); 6.67(1H, d); 5.85(1H, dd); 4.83(1H, q); 4.16(1H, t); 3.71(1H, t); 1.49(3H, s); 1.39(3H, s).

b) (2S)-4-(3-Pyridyl)-1,2-O-isopropylidenebutane-1,2-diol

The compound from Example 39a) (2.2 g) was dissolved in ethyl acetate (30 ml) and hydrogenated for 2 hours at 3 atmospheres pressure using 10% palladium on carbon (20 mg) as catalyst. The reaction was filtered through Celite® and the residue washed with ethyl acetate. The combined filtrate and washings were concentrated under reduced pressure and the residue obtained purified by column chromatography over silica eluting with diethyl ether to give the sub-title compound as an oil (2.14 g).

MS (ESI) 208 (M+H)$^+$ $^1$H NMR (CDCl$_3$) 8.48–8.45(2H, m); 7.52(1H, dt); 7.23 (1H, dd); 4.10(1H, quintet); 4.04(1H, t); 3.55(1H, t); 2.84–2.64(2H, m); 1.94–1.80(2H, m); 1.44(3H, s); 1.36 (3H, s).

c) (2S)-4-(3-Pyridyl)-1,2-butanediol

The compound from Example 39b) (19.6 g) was dissolved in 2N hydrochloric acid (100 ml) and was stirred for 40 minutes. The mixture was neutralised with saturated aqueous sodium hydrogencarbonate solution and was concentrated under reduced pressure. The residue obtained was triturated with ethyl acetate and filtered. The residue was washed with ethyl acetate and the combined organic extracts were dried over anhydrous magnesium sulfate, filtered and concentrated under reduced pressure. The residue obtained was purified by column chromatography over silica eluting with ethyl acetate:methanol (9:1) to give the sub-title compound as an oil (13.21 g).

MS (APCI) 168 (M+H)$^+$ $^1$H NMR (CDCl$_3$) 8.44–8.40(2H, m); 7.54(1H, d); 7.22 (1H, dd); 3.73–3.67(1H, m); 3.65(1H, dd); 3.48(1H, dd); 2.90–2.70(2H, bm); 2.87–2.68(2H, m); 1.84–1.67(2H, m).

d) (2S)-2-(4-Bromophenoxy)-3-tert-butyldimethylsilyloxy-4-(pyridin-3-yl)butane

A solution of (2S)-4-(3-pyridyl)-1,2-butanediol (Example 39c), 10.0 g) and 1,1'-carbonyldiimidazole (12 g) in chloroform (250 ml) was stirred at room temperature overnight. The reaction was concentrated under reduced pressure and then purified by passing through a plug of silica to remove baseline material. The residue after concentration under reduced pressure (10 g) was dissolved in dimethylformamide (100 ml). Solid 4-bromophenol (11.6 g) and cesium carbonate (16.6 g) were added and the mixture heated at 100° C. for 18 hours. The reaction mixture was acidified with aqueous hydrochloric acid (2M, 150 ml) and then extracted with ether (150 ml). The aqueous phase was then basified (to pH 9) with aqueous sodium hydroxide (2M). The aqueous phase was extracted with ethyl acetate (3×200 ml), the combined organic extracts dried over anhydrous magnesium sulfate, filtered and concentrated under reduced pressure. The residue was dissolved in dimethylformamide (10 ml) and then imidazole (6 g) followed by tert-butyldimethylsilyl chloride (8.4 g) were added. After stirring at room temperature overnight the reaction was diluted with water (200 ml) and extracted with ether:isohexane (1:1) (2×150 ml). The combined organic extracts were dried over anhydrous magnesium sulfate, filtered and concentrated under reduced pressure. The residue was purified by column chromatography over silica eluting with ether:isohexane (1:1) to give the sub-title compound as an oil (13.27 g).

MS (APCI) 436,438 (M+H)$^+$ $^1$H NMR (CDCl$_3$) 8.47(1H, d); 8.44(1H, dd); 7.51(1H, dt); 7.37(2H, d); 7.20(1H, dd); 6.76(2H, d); 4.07(1H, quintet); 3.9–3.75(2H, m); 2.9–2.6(2H, m); 2.0–1.8(2H, m); 0.92(9H, s); 0.13(3H, s); 0.09(3H, s).

e) (2S)-5(4-(2-Hydroxy-4-pyridin-3-yl-butoxy)phenyl)thiophene-2-sulfonic acid amide A solution of tert-butyllithium (15 ml, 1.7M in pentane) was added over 45 minutes to a solution of (2S)-2-(4-bromophenoxy)-3-tert-butyldimethylsilyloxy-4-(pyridin-3-yl)butane (Example 39d), 5.0 g) and triisopropylborate (6.5 ml) in tetrahydrofuran (75 ml) at −78° C. The resulting solution was stirred at −78° C. for 1 hour and was then quenched by the addition of a saturated solution of aqueous ammonium chloride in water (100 ml). The aqueous phase was saturated with sodium chloride and the mixture extracted with ethyl acetate. The combined extracts, were dried over anhydrous magnesium sulfate, filtered and concentrated under reduced pressure. The residue was purified by chromatography on silica eluting with ethyl acetate then ethyl acetate:methanol (5:1) to give (1S,2R)-4-[2-(tert-butyldimethylsilanyloxy)-1-methyl-4-pyridin-3-yl-butoxy] benzeneboronic acid (4.06 g). The boronic acid (2.0 g), 2M aqueous sodium carbonate (5 ml) and tetrakis (triphenylphosphine)palladium(0) (0.21 g) were added to a solution of 5-bromothiophene-2-sulfonic acid amide (1.80 g) in ethanol (30 ml). The mixture was heated at 100° C. for 4 hours. The mixture was cooled to room temperature and then concentrated under reduced pressure. The reaction mixture was filtered through a short silica column eluting with acetone. The filtrate was concentrated under reduced pressure and the residue purified by column chromatography eluting with ethyl acetate to give an oil (3.13 g). This was dissolved in methanol (50 ml), 2M hydrochloric acid (20 ml) was added and the solution stirred overnight at room temperature. A solid had precipitated. The solution was neutralised with solid sodium hydrogen carbonate and then concentrated under reduced pressure. Ethanol (50 ml) was added and the mixture filtered. The solid was washed with water (100 ml) and ether (200 ml) to leave a solid (1.60 g). This solid was boiled in ethanol (150 ml) for 20 minutes. After cooling the insoluble material was collected by filtration to give the title compound as a solid (1.37 g).

m.p. 197–199° C.

MS (APCI) 405 (M+H)$^+$ $^1$H NMR (DMSO) 8.46(1H, s); 8.40(1H, d); 7.66–7.61 (5H, m); 7.50(1H, d); 7.38(1H, d); 7.32–7.29(1H, m); 7.02 (2H, d); 5.08(1H, bs); 3.93(2H, d); 3.79–3.78(1H, m); 2.82–2.77(1H, m); 2.71–2.66(1H, m); 1.86–1.82(1H, m); 1.74–1.70(1H, m).

EXAMPLE 40

(1S,2R)-5-Chloro-3-[4-(2-hydroxy-1-methyl-4-pyridin-3-yl-butoxy)-phenyl]-1H-pyridin-2-one

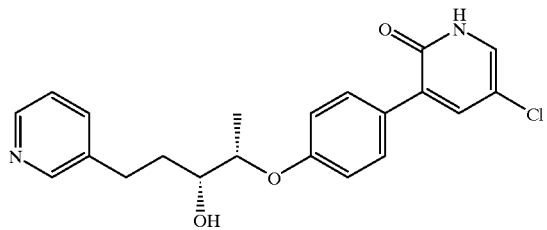

Prepared according to the method outlined in example 21b) from 2M aqueous sodium carbonate (0.75 ml), (1S, 2R)-4-(2-hydroxy-1-methyl-4-pyridin-3-ylbutoxy) benzeneboronic acid (Example 21a), 0.20 g), 3-bromo-5-chloropyrid-2-one (0.208 g, J. Org. Chem. 1992, 57(6), 1930) and tetrakis(triphenylphosphine)palladium(0) (0.025 g). Crude product was purified by normal-phase HPLC eluting with 0–25% ethanol in dichloromethane to afford the title compound as a glass (0.108 g).

MS (APCI) 385 (M+H)$^+$ $^1$H NMR (CDCl$_3$) 8.51 (1H, d); 8.46 (1H, dd); 7.64 (2H, d); 7.56 (1H, d); 7.50 (1H, d); 7.34 (1H, d); 7.23 (1H, dd);

6.95 (2H, d); 4.43–4.36 (1H, m); 3.89–3.83 (1H, m); 3.00–2.91 (1H, m); 2.79–2.68 (1H, m); 2.29 (1H, br); 1.89–1.82 (2H, m); 1.30 (3H, d).

EXAMPLE 41

(2R)-5(4-(2-Hydroxy-4-pyridin-3-yl-butanthio)phenyl) thiophene-2-sulfonic acid amide hydrochloride

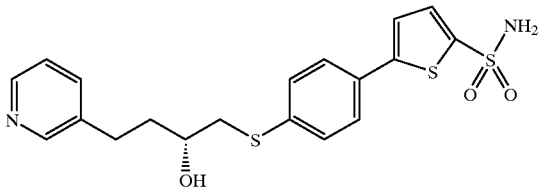

a) (2R)-1-(4-Bromothiophenoxy)-4-(pyridin-3-yl)-2-butanol

Cesium carbonate (1.3 g) and 4-bromothiophenol (0.756 g) were added to a solution of (4R)-4-[2-(pyridin-3-yl)ethyl]-1,3-dioxin-2-one (0.772 g, Example 14a)) in dry dimethylformamide (5 ml) and stirred at room temperature for 48 hours. The reaction mixture was poured into water (20 ml) and extracted three times with ethyl acetate. The combined organic phases were extracted twice with 2M hydrochloric acid. The combined aqueous extracts were basified by dropwise addition of 2M aqueous sodium hydroxide and the aqueous solution was then extracted three times with ethyl acetate. The organic extracts were combined and dried over anhydrous magnesium sulfate, filtered and concentrated under reduced pressure. The residue was purified by normal-phase HPLC eluting with ethyl acetate to give the sub-titled compound (0.67 g).

MS (APCI) 340, 342 (M+H)$^+$ $^1$H NMR (CDCl$_3$) 8.45 (1H, d); 8.44 (1H, d); 7.48 (1H, dt); 7.41 (2H, d); 7.26–7.18 (3H, m); 3.71–3.62 (1H, m); 3.11 (1H, dd), 2.87 (1H, dd); 2.84–2.79 (1H, m); 2.74–2.64 (1H, m); 2.49 (1H, d); 1.84 (2H, dt).

b) (2R)-2-(4-Bromothiophenoxy)-3-tert-butyldimethylsilyloxy-4-(pyridin-3-yl)butane tert-Butyldimethylsilyl chloride (0.452 g), followed by imidazole (0.408 g) were added to a solution of (2R)-1-(4-bromothiophenoxy)-4-(pyridin-3-yl)-2-butanol (Example 41a), 0.67 g) in anhydrous dichloromethane (20 ml), under an inert atmosphere. The mixture was stirred overnight at room temperature. The precipitate was filtered off and the filtrate was concentrated under reduced pressure. The residue was purified by column chromatography over silica eluting with hexane:ethyl acetate (1:9 to 1:1) to give the sub-title compound as an oil (0.76 g).

MS (APCI) 453,454 (M+H)$^+$ $^1$H NMR (CDCl$_3$) 8.45(1H, d); 8.43(1H, dd); 7.46 (1H, dt); 7.40 (2H, d); 7.22–7.17 (3H, m); 3.89–3.86 (1H, m); 3.02 (2H, dq); 2.78–2.58 (2H, m); 2.01–1.94 (1H, m); 1.92–1.78 (1H, m); 0.91 (9H, s); 0.05 (3H, s); 0.04 (3H, s).

c) (2R)-4-[2-(tert-Butyldimethylsilanyloxy)-4-pyridin-3-ylbutan-2-thioxyl]benzeneboronic acid A solution of tert-butyllithium (2.21 ml, 1.7M in pentane) was added over a 30 minute period to a solution of (2R)-2-(4-bromothiophenoxy)-3-tert-butyldimethylsilyloxy-4-pyridin-3-ylbutane (Example 41b), 0.76 g) and triisopropylborate (0.91 ml) in tetrahydrofuran (10 ml) at –78° C. The resulting solution was stirred at –78° C. for 1 hour and was then quenched by the addition of a saturated solution of ammonium chloride in water (50 ml). The mixture was poured into water (50 ml) and extracted into ethyl acetate (2×50 ml). The combined extracts were dried over anhydrous magnesium sulfate, filtered and concentrated. The residue was purified by chromatography on silica eluting with ethyl acetate and then ethyl acetate:methanol (5:1) to afford the sub-title compound as a foam (0.11 g).

MS (APCI) 418 (M+H)$^+$ $^1$H NMR (DMSO-D6+D$_2$O) 8.42–8.38(2H, m); 7.70 (2H, d); 7.59 (1H, dt); 7.34 (1H, dt); 7.28 (2H, d); 3.90 (1H, p); 3.15 (2H, dq), 2.71–2.60 (2H, m); 1.95–1.82 (2H, m); 0.87 (9H, s); 0.02 (3H, s); 0.00 (3H, s).

d) (2R)-5(4-(2-Hydroxy-4-pyridin-3-yl-butanthio)phenyl) thiophene-2-sulfonic acid amide hydrochloride 2M Aqueous sodium carbonate (0.24 ml), (2R)-4-[2-(tert-butyldimethylsilanyloxy)-4-pyridin-3-ylbutan-2-thioxy]benzeneboronic acid (Example 41c), 0.10 g), and tetrakis(triphenylphosphine)palladium(0) (0.01 g) were added to a solution of 5-bromothiophene-2-sulfonic acid amide (0.087 g) in ethanol (3 ml). The mixture was heated at 90° C. for 4 hours. The mixture was cooled to room temperature and solvents were evaporated under reduced pressure. The reaction mixture was triturated with acetone (10 ml) and filtered through a short silica gel column. The column was eluted with a further 10 ml of acetone. The filtrate was evaporated before purification by normal-phase HPLC, eluting with a gradient of 0–10% ethanol in dichloromethane. The colourless oil obtained was dissolved in methanol (3 ml), concentrated hydrochloric acid (0.2 ml) was added and the solution stirred at room temperature for 2 hours. The mixture was diluted with ether (10 ml) and the product was filtered off to give the title compound as a solid (0.075 g).

m.p. 208–211° C.

MS (APCI) 421 ((M-HCl)+H)$^+$ $^1$H NMR (DMSO) 8.76(1H, d); 8.70(1H, d); 8.33 (1H, d); 7.87 (1H, dd); 7.73 (2H, s); 7.62 (2H, d); 7.51 (2H, dd); 7.38 (2H, d); 3.65–3.60 (1H, m); 3.08 (2H, d); 2.99–2.84 (2H, m); 1.98–1.93 (1H, m); 1.82–1.73 (1H, m).

EXAMPLE 42

(1S,2R)-4-[4-(2-Hydroxy-1-methyl-4-pyridin-3-yl-butoxy)-phenyl]-thiophene-2-sulfonic acid amide

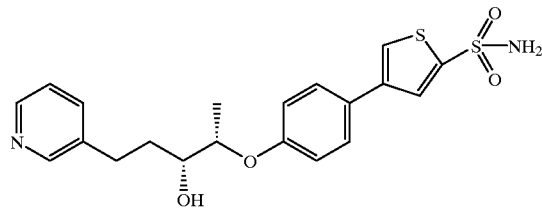

a) 4-Bromothiophene-2-sulfonamide

Zinc dust (0.98 g) was added to a stirred suspension of 4,5-dibromothiophene-2-sulfonamide (for preparation of see: J. Med. Chem. 1981, 24(8), 959) in acetic acid (3 ml) and water (8 ml) and the resulting suspension stirred at 100° C. for 30 minutes. The resulting solution was cooled, diluted with water (20 ml) and filtered. The resulting solid was redissolved in ethyl acetate (30 ml), dried over anhydrous magnesium sulfate, filtered and concentrated to afford the sub-titled compound as a solid (1.61 g).

m.p. 128–130° C.

MS (APCI) 240, 242 (M–H)$^+$ $^1$H NMR (DMSO) 7.97(1H, d); 7.81(2H, s); 7.54(2H, s).

b) (1S,2R)-4-[4-(2-Hydroxy-1-methyl-4-pyridin-3-yl-butoxy)-phenyl]-thiophene-2-sulfonic acid amide Prepared by the method outlined in Example 15g) from (1S,2R)-4-[2-(tert-butyldimethylsilanyloxy)-1-methyl-4-pyridin-3-yl-butoxy]benzeneboronic acid (0.200 g, example 15f)), 4-bromothiophene-2-sulfonic acid amide (0.145 g, Example 42a)), 2M aqueous sodium carbonate (0.5 ml) and tetrakis(triphenylphosphine)palladium(0) (0.025 g) in ethanol (3 ml). The mixture was heated at 90° C. for 4 hours and after cooling to room temperature the mixture was concentrated under reduced pressure. The residue was purified by column chromatography over silica eluting with ethyl acetate to afford the title compound as a solid (0.134 g).

m.p. 151–152.5° C.

MS (APCI) 419 (M+H)$^+$ $^1$H NMR (DMSO-D6) 8.44 (1H, d); 8.38 (1H, dd); 7.99 (1H, d); 7.86 (1H, d); 7.69 (2H, s); 7.65–7.62 (1H, m); 7.59 (2H, d); 7.29 (1H, dd); 6.97 (2H, d); 4.99 (1H, d); 4.32 (1H, dq), 3.59–3.52 (1H, m); 2.84–2.78 (1H, m); 2.74–2.60 (1H, m); 1.88–1.79 (1H, m); 1.72–1.58 (1H, m); 1.23 (3H, d).

Pharmacological Activity

The pharmacological activity of the compounds of the invention may be tested by the method of E. Wells et al, 'Characterization of primate bronchoalveolar mast cells: II—inhibition of histamine, LTC$_4$ and PGD$_2$ release from primate bronchoalveolar mast cells and a comparison with rat peritoneal mast cells', *J. Immunol.*, vol. 137, 3941, 1986.

The compounds of examples 1 to 42 were tested and found to inhibit histamine release at a concentration of less than 10$^{-5}$ M (IC$_{50}$).

What is claimed is:

1. A compound of formula I:

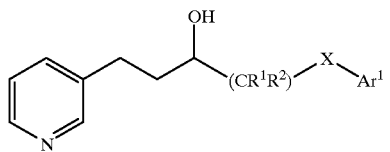

(I)

wherein;

X is O, S or CH$_2$;

R$^1$ and R$^2$ are independently hydrogen, C$_{1-6}$ alkyl or C$_{3-6}$ cycloalkyl or R$^1$ and R$^2$ together with the carbon atom to which they are attached form a C$_{3-6}$ cycloalkyl group; Ar$^1$ is a fused bicyclic ring system containing one or more heteroatoms, a fused tricyclic ring system optionally containing an oxygen atom, or Ar$^1$ is a group R$^3$—R$^4$ where one of R$^3$/R$^4$ is a phenyl ring and the other is a 5- or 6-membered heterocyclic ring containing one or more heteroatoms, each Ar$^1$ group being optionally substituted by halo, nitro, C$_{1-6}$ alkyl (optionally substituted by one or more fluorine atoms), CN, —Y—NR$^6$C(O)NR$^7$—R$^8$, —O—Y—C(O)NR$^7$R$^8$, —O—Y—C(S)NR$^7$R$^8$, —Y—C(O)NR$^7$R$^8$, —Y—C(S)NR$^7$R$^8$, —Y—SO$_2$NR$^7$R$^8$, —Y—NR$^7$R$^8$, SO$_2$NR$^7$R$^8$, C(O)NR$^7$R$^8$, C(S)NR$^7$R$^8$, C(O)R$^9$, —OC(O)R$^9$, —Y—OR$^9$, —Y—CO$_2$R, —Y—NR$^{10}$C(O)NR$^{11}$—Z—R$^{12}$, SO$_2$NR$^{10}$, C(O)NR$^7$R$^8$, —Y—SO$_2$NHNR$^7$R$^8$, —Y—C(O)NR$^{11}$—Z—R$^{12}$, —Y—C(S)NR$^{11}$—Z—R$^{12}$, N(R$^{10}$)SO$_2$R$^{11}$, N(R$^{10}$)C(O)R$^{11}$ or N(R$^{10}$)CO$_2$R$^{11}$ where:

Y is a bond, C$_{1-6}$ alkylene or C$_{2-6}$ alkenylene;

R$^7$ and R$^8$ are independently hydrogen or C$_{1-6}$ alkyl or together with the nitrogen atom to which they are attached form an optionally substituted 5- to 7-membered heterocyclic ring optionally containing a further heteroatom selected from nitrogen, oxygen or sulfur; R$^5$, R$^6$, R$^9$, R$^{11}$ and R$^{10}$ are independently hydrogen or C$_{1-10}$ alkyl (optionally substituted by one or more fluorine atoms);

Z is C$_{1-6}$ alkylene; and

R$^{12}$ is a group NR$^{10}$C(O)R$^{11}$, NR$^{10}$CO$_2$R$^{11}$, OR$^5$, NR$^7$R$^8$ or CO$_2$R$^{13}$ where R$^5$, R$^7$, R$^8$, R$^{10}$ and R$^{11}$ are as defined above and R$^{13}$ is hydrogen, C$_{1-6}$ alkyl, C$_{1-6}$ alkylaryl or aryl optionally substituted by hydroxy, or a salt or solvate thereof, provided that R$^4$ is not thiazinyl, thiazolyl or alkyl substituted thiazolyl, and provided that when R$^4$ is a pyridyl ring, said ring has one or more substituents as defined above other than alkyl groups.

2. A compound according to claim 1 in which X is O.

3. A compound according to claim 1 in which R$^1$ and R$^2$ are both hydrogen or one is hydrogen and the other is methyl.

4. A compound according to claim 1 in which Ar$^1$ is a group R$^3$—R$^4$.

5. A compound according to claim 4 where R$^3$ is phenyl and R$^4$ is thiophene substituted by cyano, halo, sulphonamido or methyl.

6. A compound according to claim 1 which is;

(±)-1-(2,3-Dihydro-benzo[1,4]dioxin-6-yl)-5-pyridin-3-yl-pentan-3-ol, (±)-1-(2,3-Dihydro-benzo[1,4]dioxin-6-yloxy)-4-pyridin-3-yl-butan-2-ol, (±)-1-([9H]-Fluoren-2-yloxy)-4-pyridin-3-yl-butan-2-ol, (±)-1-(Dibenzofuran-3-yloxy)-4-pyridin-3-yl-butan-2-ol, (2R)-1-[4-(5-Chloro-thiophen-2-yl)-phenoxy]-4-pyridin-3-yl-butan-2-ol, (±)-1-(Benzofuran-6-yloxy)-4-pyridin-3-yl-butan-2-ol, (2R)-5-[4-(2-Hydroxy-4-pyridin-3-yl-butoxy)-phenyl]-1,3-dimethyl-1H-pyrimidine-2,4-dione, (2R)-1-[4-(2,4-Dimethoxy-pyrimidin-5-yl)phenoxy]-4-pyridin-3-yl-butan-2-ol, (2R)-5-[4-(2-Hydroxy-4-pyridin-3-yl-butoxy)-phenyl]-1H-pyrimidine-2,4-dione, (2R)-4-[4-(2-Hydroxy-4-pyridin-3-yl-butoxy)phenyl]-1H-pyridin-2-one, (2R)-5-[4-(2-Hydroxy-4-pyridin-3-yl-butoxy)-phenyl]-1H-pyridin-2-one, (2R)-4-[4-(2-Hydroxy-4-pyridin-3-yl-butoxy)-phenyl]-1-methyl-1H-pyridin-2-one, (2R)-5-[4-(2-Hydroxy-4-pyridin-3-yl-butoxy)phenyl]-1-methyl-1H-pyridin-2-one, (2R)-1-(4-[1,3,4]-Oxadiazol-2-ylphenoxy)-4-pyridin-3-yl-butan-2-ol, (2S,3R)-2-(4-(2,4-Dimethoxypyrimidin-5-yl)phenoxy)-5-pyridin-3-yl-pentan-3-ol, (1S,2R)-5-[4-(2-Hydroxy-1-methyl-4-pyridin-3-yl-butoxy)-phenyl]-1H-pyridin-2-one, (1S,2R)-5-[4-(2-Hydroxy-1-methyl-4-pyridin-3-ylbutoxy)phenyl]-1-methyl-1H-pyridin-2-one, (3R,4S)-4-[4-(6-Dimethylaminopyridin-2-yl)-phenoxy]-1-pyridin-3-ylpentan-3-ol, (2R)-1-[4-(6-Dimethylaminopyridin-2-yl)phenoxy]-4-pyridin-3-ylbutan-2-ol, (2R)-5-[4-(2-Hydroxy-4-pyridin-3-ylbutoxy)phenyl]thiophene-2-sulfonic acid amide, (1S,2R)-5-[4-(2-Hydroxy-1-methyl-4-pyridin-3-yl-butoxy)-phenyl]-thiophene-2-sulfonic acid amide, (3R,4S)-4-[4-(2-Methoxypyridin-3-yl)phenoxy]-1-pyridin-3-yl-pentan-3-ol, (3R,4S)-4-[4-(2-Dimethylaminopyridin-3-yl)phenoxy]-1-pyridin-3-ylpentan-3-ol,
(3R,4S)-4-[4-(2-Methoxypyridin-4-yl)phenoxy]-1-pyridin-3-yl-pentan-3-ol,
(1S,2R)-5-[4-(2-Hydroxy-1-methyl-4-pyridin-3-yl-butoxy)phenyl]nicotinonitrile,
(2R)-5-[4-(2-Hydroxy-4-pyridin-3-yl-butoxy)phenyl]nicotinonitrile,
(3R,4S)-4-[4-(6-Methoxy-pyridin-2-yl)-phenoxy]-1-pyridin-3-yl-pentan-3-ol,
(2R)-1-[4-(6-Methoxy-pyridin-2-yl)-phenoxy]-4-pyridin-3-yl-butan-2-ol,
(1S,2R)-4-[4-(2-Hydroxy-1-methyl-4-pyridin-3-yl-butoxy)phenyl]-(1H)-pyridin-2-one,
(3R,4S)-4-(4-[1,3,4]Oxadiazol-2-ylphenoxy)-1-pyridin-3-yl-pentan-3-ol,
(2R)-4-[4-(2-Hydroxy-4-pyridin-3-yl-butoxy)-phenyl]-(1H)-pyridin-2-one,
(1R,2S)-4-[4-(2-Hydroxy-1-methyl-4-pyridin-3-yl-butoxy)-phenyl]pyrazole-1-sulfonic acid dimethylamide,
(2R)-1-[4-(2-Methoxypyridin-3-yl)phenoxy]-4-pyridin-3-ylbutan-2-ol,
(2R)-4-Pyridin-3-yl-1-(4-pyrimidin-5-yl-phenoxy)butan-2-ol,
(3R,4S)-1-Pyridin-3-yl-4-(4-pyrimidin-5-yl-phenoxy)pentan-3-ol,
(1S,2R)-5-[4-(2-Hydroxy-1-methyl-4-pyridin-3-yl-butoxy)phenyl]-1-methyl-3-trifluoromethyl-1H-pyridin-2-one,
(2R)-5-[4-(2-Hydroxy-4-pyridin-3-yl-butoxy)-phenyl]-1-methyl-3-trifluoromethyl-1H-pyridin-2-one,
(3R,4S)-4-[4-(4-Chloro-2-methylamino-pyrimidin-5-yl)-phenoxy]-1-pyridin-3-yl-pentan-3-ol,
(2S)-5(4-(2-Hydroxy-4-pyridin-3-yl-butoxy)phenyl) thiophene-2-sulfonic acid amide,
(1S,2R)-5-Chloro-3-[4-(2-hydroxy-1-methyl-4-pyridin-3-yl-butoxy)-phenyl]-1H-pyridin-2-one,
(2R)-5(4-(2-Hydroxy-4-pyridin-3-yl-butanthio)phenyl) thiophene-2-sulfonic acid amide,
(1S,2R)-4-[4-(2-Hydroxy-1-methyl-4-pyridin-3-yl-butoxy)-phenyl]-thiophene-2-sulfonic acid amide,
or salts or solvates thereof.

7. A pharmaceutical composition comprising a compound of formula I or a salt or solvate hereof as defined in claim 1 in association with a pharmaceutically acceptable adjuvant, diluent or carrier.

8. A process for the preparation of compounds of formula I as defined in claim 1 which comprises:

(a) reduction of a corresponding compound of formula (II):

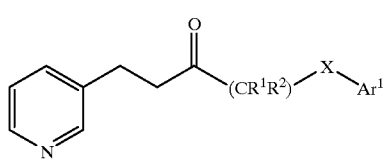

(II)

wherein $R^1$, $R^2$, X and $Ar^1$ is as defined in formula (I);

(b) for compounds of formula (I), wherein $Ar^1$ is a group $R^3$—$R^4$, forming the $R^3$—$R^4$ bond by reaction of a compound of formula (III):

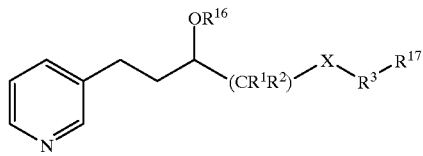

(III)

with a compound of formula (IV):

$$R^4\text{———}R^{18}$$ (IV)

where $R^1$, $R^2$, $R^3$, $R^4$ and are as defined in formula (I), $R^{16}$ is a hydroxy protecting group, and one of $R^{17}/R^{18}$ is triflate or halo and the other is $B(OH)_2$, or ZnHal, or (c) for compounds of formula (I) where $R^1$ and $R^2$ are both hydrogen, reaction of (±)-3-(2-oxiranylethyl) pyridine or α-(chloromethyl)-3-pyridinepropanol either with a compound of formula (V):

$$MYAr^1$$ (V)

where Y is O, S or $CH_2$, M is Li, Na, K, Cs or MgHal where Hal is halogen and $Ar^1$ is as defined in formula (I);

or with a compound of formula (VI):

$$HYAr^1$$ (VI)

where Y is as defined in formula (V) in the presence of a base; or (d) for compounds of formula (I), where $R^1$ and $R^2$ are both hydrogen, and X represents O or S, reaction of a compound of formula (V) or (VI), as hereinbefore defined, with a suitably protected and activated derivative of 4-(3-pyridyl)-1,2-butanediol; or (e) preparation of compounds of formula (I) wherein X represents O, from a compound of formula (VII):

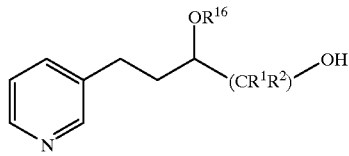

(VII)

in which $R^3$, $R^4$, and $R^{16}$ are as defined in process (b) by reaction with a compound of formula (VI) wherein Y represents O, and optionally thereafter process (a) to (e):

removing any protecting groups forming a pharmaceutically acceptable salt or solvate.

9. A method of treating an inflammatory condition in a patient in need of such treatment, comprising the step of administering to said patient an effective amount of a compound of formula (I) as claimed in claim 1.

10. A method of treating an allergic condition in a patient in need of such treatment, comprising the step of administering to said patient an effective amount of a compound of formula (I) as claimed in claim 1.

11. A method of treating an auto-immune condition in a patient in need of such treatment, comprising the step of administering to said patient an effective amount of a compound of formula (I) as claimed in claim 1.

* * * * *